United States Patent
Hu et al.

(10) Patent No.: US 12,182,970 B2
(45) Date of Patent: Dec. 31, 2024

(54) X-RAY IMAGING RESTORATION USING DEEP LEARNING ALGORITHMS

(71) Applicant: CANON MEDICAL SYSTEMS CORPORATION, Otawara (JP)

(72) Inventors: Yi Hu, Vernon Hills, IL (US); Rui Hua, Vernon Hills, IL (US); Joseph Manak, Vernon Hills, IL (US); John Baumgart, Vernon Hills, IL (US); Yu-Bing Chang, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 182 days.

(21) Appl. No.: 17/356,612

(22) Filed: Jun. 24, 2021

(65) Prior Publication Data
US 2022/0414832 A1    Dec. 29, 2022

(51) Int. Cl.
*G06T 5/70* (2024.01)
*G06N 3/04* (2023.01)
(Continued)

(52) U.S. Cl.
CPC ............... *G06T 5/70* (2024.01); *G06N 3/04* (2013.01); *G06N 3/082* (2013.01); *G06T 5/73* (2024.01);
(Continued)

(58) Field of Classification Search
CPC ............ G06T 5/002; G06T 5/003; G06T 2207/10116; G06T 2207/20081;
(Continued)

(56) References Cited

U.S. PATENT DOCUMENTS 10,173,537 B2 * 1/2019 Herzog ................ B60L 53/16
10,290,084 B1 * 5/2019 Podilchuk .............. G06T 5/50
(Continued)

FOREIGN PATENT DOCUMENTS

CA    2 729 607 A1    1/2010
EP    3 367 329 B1    4/2020
(Continued)

OTHER PUBLICATIONS

Shuang Zhang, et al., "Deep Motion Blur Removal Using Noisy/Blurry Image Pairs", Computer Science, Computer Vision and Pattern Recognition, Image and Video Processing, arXiv:1911.08541v2, Nov. 25, 2019, pp. 1-10.
(Continued)

*Primary Examiner* — Jose L Couso
(74) *Attorney, Agent, or Firm* — Oblon, McClelland, Maier & Neustadt, L.L.P.

(57) ABSTRACT

A general workflow for deep learning based image restoration in X-ray and fluoroscopy/fluorography is disclosed. Higher quality images and lower quality images are generated as training data. This training data can further be categorized by anatomical structure. This training data can be used to train a learned model, such as a neural network or deep-learning neural network. Once trained, the learned model can be used for real-time inferencing. The inferencing can be more further improved by employing a variety of techniques, including pruning the learned model, reducing the precision of the learned mode, utilizing multiple image restoration processors, or dividing a full size image into snippets.

24 Claims, 17 Drawing Sheets

(51) Int. Cl.
  *G06N 3/082* (2023.01)
  *G06T 5/73* (2024.01)
  *G16H 30/20* (2018.01)
  *A61B 6/00* (2006.01)

(52) U.S. Cl.
  CPC ............ *G16H 30/20* (2018.01); *A61B 6/5258* (2013.01); *G06T 2207/10116* (2013.01); *G06T 2207/20081* (2013.01); *G06T 2207/20084* (2013.01); *G06T 2207/30004* (2013.01)

(58) Field of Classification Search
  CPC ........... G06T 2207/20084; G06T 2207/30004; G06T 2207/10072; G06T 3/4046; G06T 9/002; G06T 2207/20076; G06N 3/04; G06N 3/082; G06N 3/02; G06N 3/08–088; G06N 3/0445; G06N 3/0454; G06N 3/4046; G06N 7/00; G06N 20/00; G16H 30/20; A61B 6/5258; A61B 6/42; A61B 6/5205; A61B 6/586; A61B 6/585; A61B 6/48; G06K 7/1482; G06V 10/454; G06V 10/54; G06V 10/774; G06V 10/82; G06V 30/18057; G06V 10/30; G06V 2201/03; Y10S 128/925; G06F 18/214
  See application file for complete search history.

(56) References Cited

U.S. PATENT DOCUMENTS

| | | | | |
|---|---|---|---|---|
| 10,453,570 | B1* | 10/2019 | Podilchuk | G16H 50/70 |
| 10,621,379 | B1 | 4/2020 | Kim | |
| 10,713,537 | B2* | 7/2020 | Heide | G06V 10/764 |
| 11,120,582 | B2* | 9/2021 | Zhou | G06N 20/20 |
| 11,127,117 | B2* | 9/2021 | Alletto | G06T 5/002 |
| 2017/0372193 | A1* | 12/2017 | Mailhe | G06T 5/005 |
| 2018/0240219 | A1* | 8/2018 | Mentl | G06T 11/008 |
| 2018/0268526 | A1 | 9/2018 | Mentl et al. | |
| 2018/0268533 | A1* | 9/2018 | Mech | G06T 7/0002 |
| 2018/0336709 | A1* | 11/2018 | Persson | G06T 11/006 |
| 2019/0104940 | A1* | 4/2019 | Zhou | G06T 11/008 |
| 2019/0303720 | A1* | 10/2019 | Karam | G06F 18/22 |
| 2020/0065940 | A1* | 2/2020 | Tang | G06F 18/214 |
| 2020/0311878 | A1 | 10/2020 | Matsuura et al. | |
| 2021/0007702 | A1 | 1/2021 | Lee et al. | |
| 2021/0034921 | A1* | 2/2021 | Pinkovich | G06N 3/082 |
| 2021/0118098 | A1 | 4/2021 | Chan et al. | |
| 2021/0152735 | A1* | 5/2021 | Zhou | G06T 5/001 |
| 2021/0264574 | A1* | 8/2021 | Podilchuk | G06T 7/13 |
| 2021/0264602 | A1* | 8/2021 | Podilchuk | G06F 18/40 |
| 2023/0033442 | A1* | 2/2023 | Xiang | G06T 3/4053 |

FOREIGN PATENT DOCUMENTS

| | | |
|---|---|---|
| WO | WO 2019/183584 A1 | 9/2019 |
| WO | WO 2020/069489 A1 | 4/2020 |
| WO | WO-2022048977 A1 * | 3/2022 |

OTHER PUBLICATIONS

Chengyang Wu, et al., "Combined spatial and temporal deep learning for image noise reduction of fluoroscopic x-ray sequences", Proceedings Spie Medical Imaging: Physics of Medical Imaging, vol. 11312, Mar. 16, 2020, 7 pages (Abstract only).

Chengyang Wu, et al., "Fluoroscopic Image Denoising with Feature Preserving Residual Noise Learning", ISICDM 2019: Proceedings of the Third International Symposium on Image Computing and Digital Medicine, Aug. 24, 2019, pp. 97-101 (Abstract only).

Alex Krizhevsky, et al., "ImageNet Classification with Deep Convolutional Neural Networks", Advances in Neural Information Processing Systems, 2012, 9 pages.

Kai Zhang, et al., "Beyond a Gaussian Denoiser: Residual Learning of Deep CNN for Image Denoising." IEEE Transactions on Image Processing, vol. 26, Issue 7, Jul. 2017, pp. 3142-3155.

Praneeth SADDA, et al., "Real-Time Medical Video Denoising with Deep Learning: Application to Angiography", International Journal of Applied Information Systems, vol. 12, No. 13, May 2018, pp. 22-28.

Marco Pavoni, et al., "Image Denoising with Convolutional Neural Networks for Percutaneous Transluminal Coronary Angioplasty", European Congress On Computational Methods in Applied Sciences and Engineering, Eccomas, Vipimage, 2017, pp. 255-265 (Abstract only).

Marco Pavoni, et al., "Convolutional neural network-based image enhancement for x-ray percutaneous coronary intervention", Journal of Medical Imaging, vol. 5, No. 2, Apr.-Jun. 2018, pp. 024006-1-024006-12.

Yevgen Matviychuk, et al., "Learning a multiscale patch-based Representation for image denoising in X-RAY fluoroscopy", IEEE International Conference on Image Processing (ICIP), Sep. 25-28, 2016, pp. 2330-2334 (Abstract only).

Chao Dong, et al., "Image Super-Resolution Using Deep Convolutional Networks", IEEE Transactions on Pattern Analysis and Machine Intelligence, vol. 38, Issue 2, Jun. 1, 2015, pp. 295-307.

Harold C. Burger, et al., "Image denoising: Can plain Neural Networks compete with BM3D?", 2012 IEEE Conference on Computer Vision and Pattern Recognition, Jun. 16-21, 2012, pp. 4321-4328.

Jan Kuntz, et al., "Focal spot deconvolution using convolutional neural networks", Proceedings SPIE Medical Imaging: Physics of Medical Imaging, International Society for Optics and Photonics, vol. 10948, Mar. 1, 2019, 3 pages (Abstract only).

Ying Tai, et al., "Image Super-Resolution via Deep Recursive Residual Network", Proceedings of the IEEE Conference on Computer Vision and Pattern Recognition (CVPR), Jul. 21-26, 2017, pp. 3147-3155.

Partial European Search Report issued on Dec. 16, 2022, in corresponding European Patent Application No. 22180404.0, 15 pages.

Extended European Search Report issued on Mar. 20, 2023, in corresponding European Patent Application No. 22180404.0, 13 pages.

Yim D.C et al., "A deep convolutional neural network for simultaneous denoising and deblurring in computed tomography", Journal of Instrumentation, XP055982807, 2020, 12 pages.

Chen Qifeng et al., "Fast Image Processing with Fully-Convolutional Networks", 2017 IEEE International Conference on Computer Vision, XP033283116, pp. 2516-2525.

Danka Tivadar et al., "How to accelerate and compress neural networks with quantization", XP55983074, 2020, 12 pages.

* cited by examiner

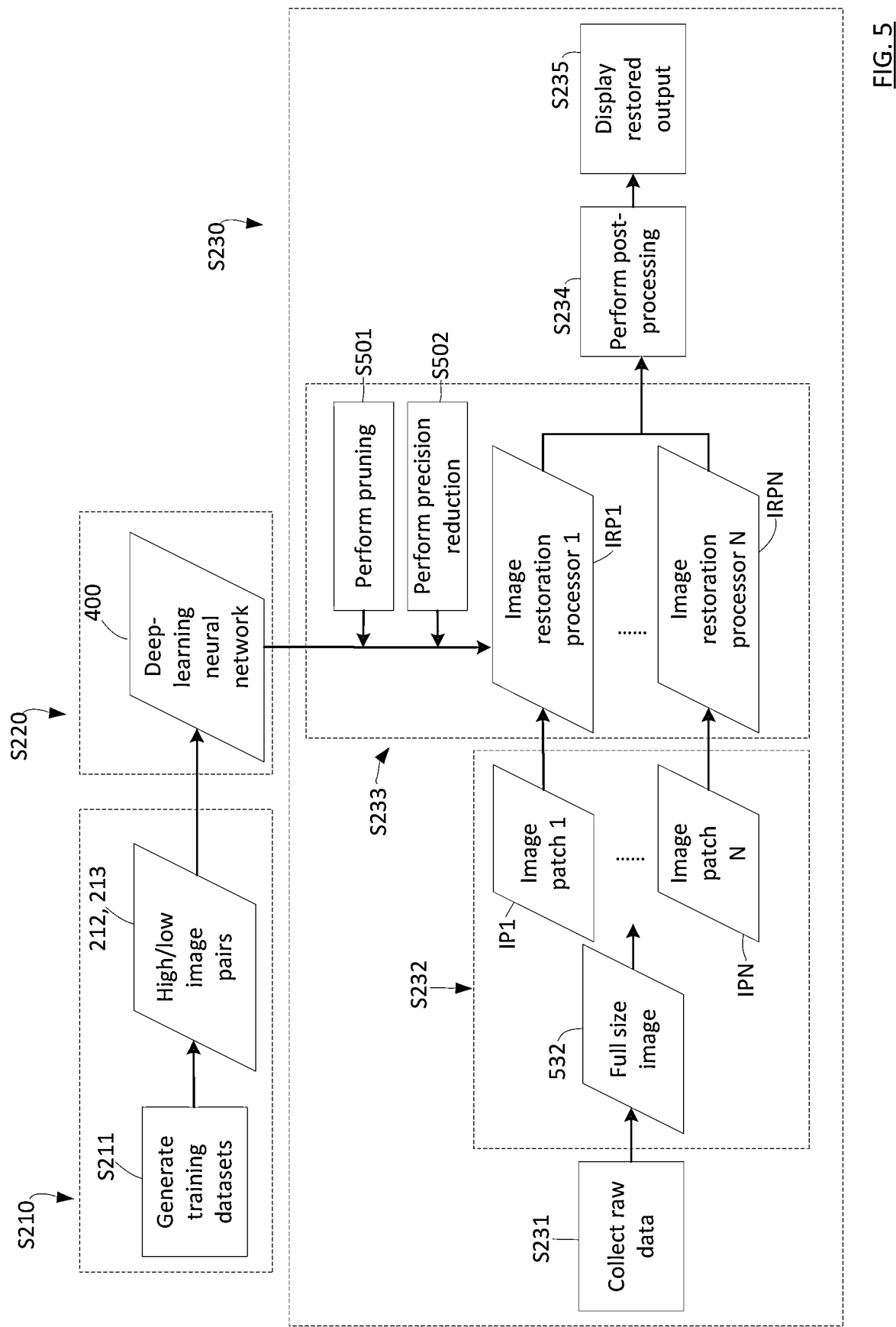

X-RAY IMAGING RESTORATION USING DEEP LEARNING ALGORITHMS

FIELD

The method and system described herein are directed to restoration of X-ray images, and in one embodiment to the restoration of X-ray images using deep learning algorithms.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

X-ray images tend to be blurry and noisy. Blurring and noise in radiography can make analyzing images difficult, and can lead to misdiagnoses. Scans using higher doses of x-rays can be used to create sharper images, but higher doses of x-rays can be dangerous for patients. On the other hand, scans performed at reduced doses come at the cost of increasing noise. This trade-off is especially apparent for time series acquisitions, where long exposure time is not possible, such as for cardiac catheterization with fluoroscopy.

Some image restoration techniques can involve reducing blur, but this comes at the cost of increasing noise. Other techniques can reduce noise, but this comes at the cost of artifacts. Further, image restoration techniques often cause unnatural textures, ringing artifacts, require hand-turning of filter parameters, are computationally expensive, and are hard to implement.

In light of the above mentioned problems, there exists a need to improve techniques related to deblurring and denoising X-ray images.

SUMMARY

In one exemplary embodiment, the present disclosure is directed to an X-ray diagnosis apparatus, comprising: processing circuitry configured to input a first image to a learned model; and output the first image with less noise and blur as a processed image, wherein the learned model is trained by using a second image as input learning data and a third image with less noise and blur than the second image as target output learning data.

In one exemplary aspect, the third image is obtained by deblurring and denoising the second image.

In one exemplary aspect, the second image is obtained by adding blur and noise to the third image.

In one exemplary aspect, the processing circuitry is further configured to prune the learned model after the learned model has been trained.

In one exemplary aspect, the processing circuitry is further configured to reduce precision of the learned model after the learned model has been trained.

In one exemplary aspect, the learned model is a deep-learning neural network.

In one exemplary aspect, the first image, the second image, and the third image are X-ray images.

In one exemplary aspect, the first image, the second image, and the third image are of a same anatomical structure.

In one exemplary aspect, the first image is a snippet of a full size image.

In one exemplary aspect, the third image is a manipulated non-medical dataset, and the second image is the manipulated non-medical dataset with corruption.

In one exemplary aspect, a second learned model is trained to take a fourth image as an input and output the third image, the second learned model trained using a manipulated non-medical dataset as output learning data, and the manipulated non-medical dataset with corruption as input learning data.

In one exemplary embodiment, the present disclosure is also directed to a method for image restoration comprising: inputting a first image to a learned model; and outputting the first image with less noise and blur as a processed image, wherein the learned model is trained by using a second image as input learning data and a third image with less noise and blur than the second image as output learning data.

In one exemplary aspect, the second image is obtained by deblurring and denoising the first image.

In one exemplary aspect, the first image is obtained by adding blur and noise to the second image.

In one exemplary aspect, the method further comprises: pruning the learned model after the learned model has been trained.

In one exemplary aspect, the method further comprises: reducing precision of the learned model after the learned model has been trained.

In one exemplary aspect, the third image is a manipulated non-medical dataset, and the second image is the manipulated non-medical dataset with corruption.

In one exemplary aspect, a second learned model is trained to take a fourth image as an input and output the third image, the second learned model trained using a manipulated non-medical dataset as output learning data, and the manipulated non-medical dataset with corruption as input learning data.

In one exemplary aspect, the first image, the second image, and the third image are of a same anatomic structure.

In one exemplary embodiment, the present disclosure is also directed a non-transitory computer-readable medium including computer-readable instructions that, when executed by a computing system, cause the computing system to process a noisy image by performing a method comprising: inputting a first image to a learned model; and outputting the first image with less noise and blur as a processed image, wherein the learned model is trained by using a second image as input learning data and a third image with less noise and blur than the second image as output learning data.

In one exemplary embodiment, the present disclosure is also directed a method for training a machine learning model, the method comprising: training the machine learning model by using a second image as input learning data and a third image with less noise and blur than the second image as output learning data, wherein the trained machine learning model receives a first image as an input image and output the first image with less noise and blur as a processed image.

BRIEF DESCRIPTION OF DRAWINGS

FIG. 5 is a workflow diagram of an X-ray image restoration process, according to one exemplary embodiment of the present disclosure;

DETAILED DESCRIPTION

Figure 1:
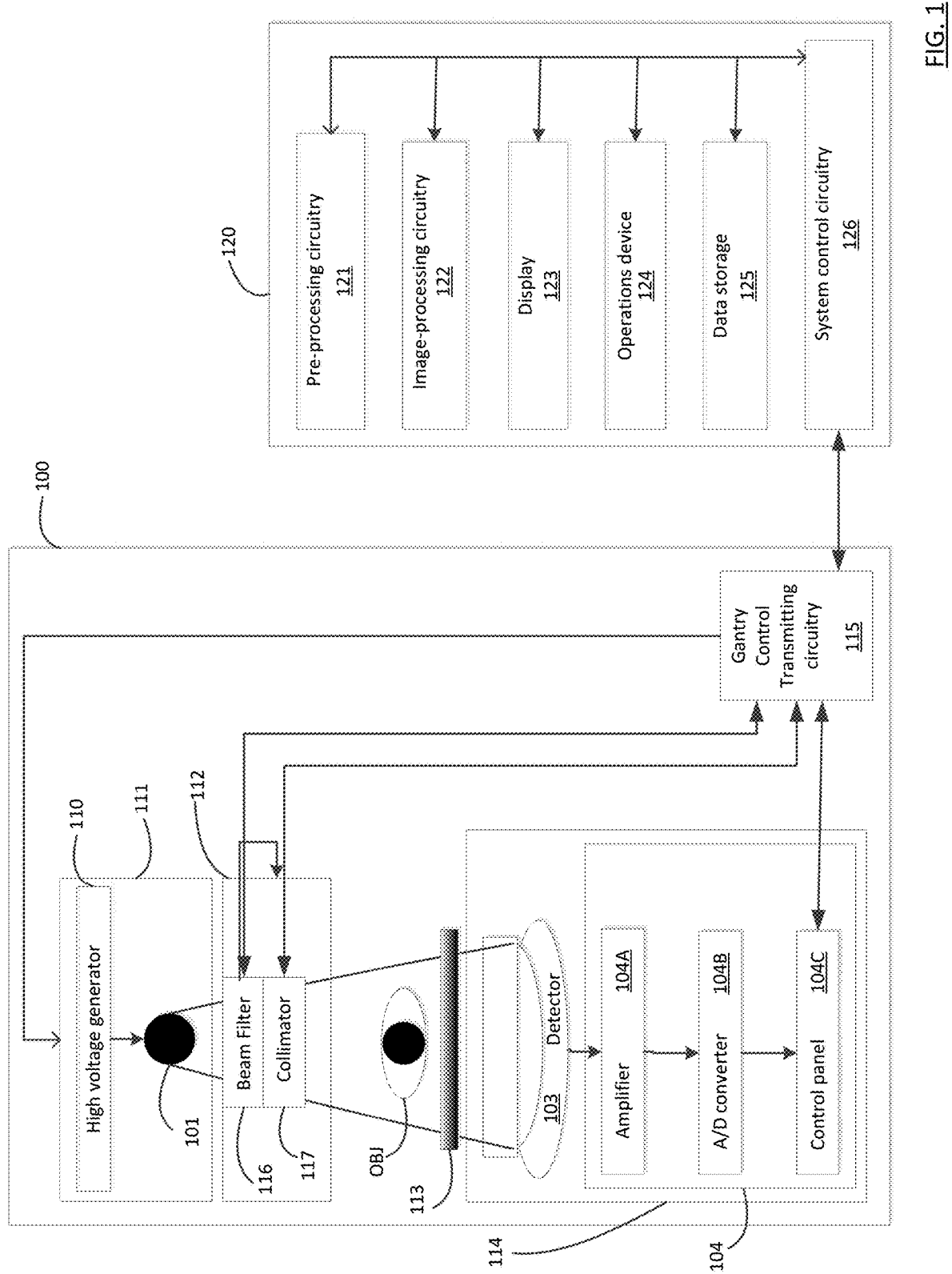
FIG. 1 is an X-ray system, according to one exemplary embodiment of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways. This disclosure describes an X-ray detector to illustrate the various embodiments, but these concepts can be applied to similar systems, such as single-photon emission computed tomography (SPECT) systems, magnetic resonance imaging (MRI) systems, ultrasound systems, computed tomography (CT) systems, PET-CT systems, etc. The imaging techniques discussed herein can be applied to any X-ray imaging technique that can generate 2D X-ray images, such as chest X-rays, mammography, and angiography. Further, as used herein, the words "a", "an" and the like generally carry a meaning of "one or more", unless stated otherwise.

This disclosure is related to a system and method for restoring images using deep learning algorithms. In one embodiment, the deep learning algorithms can include using a neural network, such as a deep-learning neural network, and the images being restored can include X-ray images. This disclosure will describe a workflow with three aspects: (i) training data preparation, (ii) the training process, and (iii) the image restoration process.

The training data preparation aspect will be described with reference to two techniques: (i) deblurring and denoising images and (ii) degrading images. The training preparation aspect will be described with respect to two exemplary techniques: (i) mapping a single lower quality image to a single higher quality image, and (ii) mapping a time series of lower quality images to a single higher quality image. The X-ray image restoration process will be described with respect to how to use the trained deep-learning neural network for real-time inferencing.

In one aspect, it can be appreciated that the present disclosure may be implemented within an X-ray apparatus. FIG. 1 is an exemplary X-ray apparatus that can be used with the disclosed techniques and structures. The X-ray apparatus includes a gantry 100 and a console 120. The gantry 100 includes an X-ray source system 111, a beam-shaping system 112, a patient table 113, a detection system 114, and a gantry control transmission circuitry 115. The X-ray source system 111 includes a high voltage generator 110 and an X-ray tube 101. The high voltage generator 110 applies a high voltage to the X-ray tube 101 under the control of the gantry control transmission circuitry 115, and supplies a filament current to the X-ray tube 101 under the control of the gantry control transmission circuitry 115. The X-ray tube 101 generates X-rays to irradiate an object OBJ (e.g., a patient) upon receiving a trigger from the high voltage generator 110. The collimation system 112 includes a beam filter/attenuator 116 which modifies the spectrum of the X-ray beam from the X-ray tube 101. A collimator 117 opens and closes in accordance with a field of view selected at the time of the operation. The collimation system 112 forms an X-ray beam and irradiates the object OBJ (e.g., a patient) with X-rays.

The detection system 114 includes a two-dimensional array of detection elements (pixels) configured to absorb the X-ray transmitted through the object OBJ (e.g., a patient) and generate an electrical charge signal proportional to the absorbed X-ray intensity. The electrical signal of each pixel is amplified and converted to a digital number by A/D converters. For example, the detection system 114 includes the detector 103 and a data acquisition system (DAS) 104. The detector 103 detects the X-rays generated from the X-ray tube 101. The detector 103 is equipped with a plurality of detection elements arrayed two-dimensionally. Each detection element detects the X-rays generated from the X-ray tube 101 and generates an electrical signal (current signal) corresponding to the intensity of the detected X-rays.

The generated electrical signal is supplied to the DAS 104. The DAS 104 includes an amplifier 104A, an A/D converter 104B, and a control panel 104C. The DAS 104 reads out electrical signals via the detector 103 and obtains the readout electrical signals, via the control panel 104C. The gantry control transmission circuitry 115 controls the high voltage generator 110, the attenuator 116, the collimator 117, and the control panel 104C to execute X-ray imaging.

The console 120 includes pre-processing circuitry 121, image-processing circuitry 122, a display 123, an operation device 124, data storage 125, and system control circuitry 126. The pre-processing circuitry 121 executes pre-processing, such as sensitivity correction for raw data supplied from the detection system 114, via the gantry control transmission circuitry 115 which can be circuitry for controlling a wired interface (e.g., serial connection circuitry (such as USB connection circuitry), Ethernet connection circuitry, optical connection circuitry) or controlling a wireless interface (e.g., any of the 802.11 families of protocols). Although the console 120 is illustrated as co-located with the gantry 100 (e.g., within the same room or in adjacent rooms), the gantry 100 and the console 120 may be remotely located from each other (e.g., in different areas of the same floor, on different floors, and in different buildings). Moreover, image processing described herein as being performed by the console 120 may be off-loaded to a secondary processing device (not shown) such as an image processing computer.

The image-processing circuitry 122 can perform the image-processing methods. The display 123 displays the image generated by the image-processing circuitry 122. The operation circuitry 124 accepts various types of commands and information inputs from a user, via an input device. The data storage (memory) 125 stores the raw data and various types of data, such as projection data and images. In addition, the data storage 125 stores control programs for the X-ray apparatus, and control programs for performing the image-processing methods described herein. The system control circuitry 126 functions as the main circuitry of the X-ray apparatus. The system control circuitry 126 reads out control programs stored in the data storage 125 and loads the programs into the memory. The system control circuitry 126 controls the respective circuitry in the X-ray apparatus in accordance with the loaded control programs. The system control circuitry 126 can be configured to run any of the methods and workflows described in the present disclosure.

Figure 2:
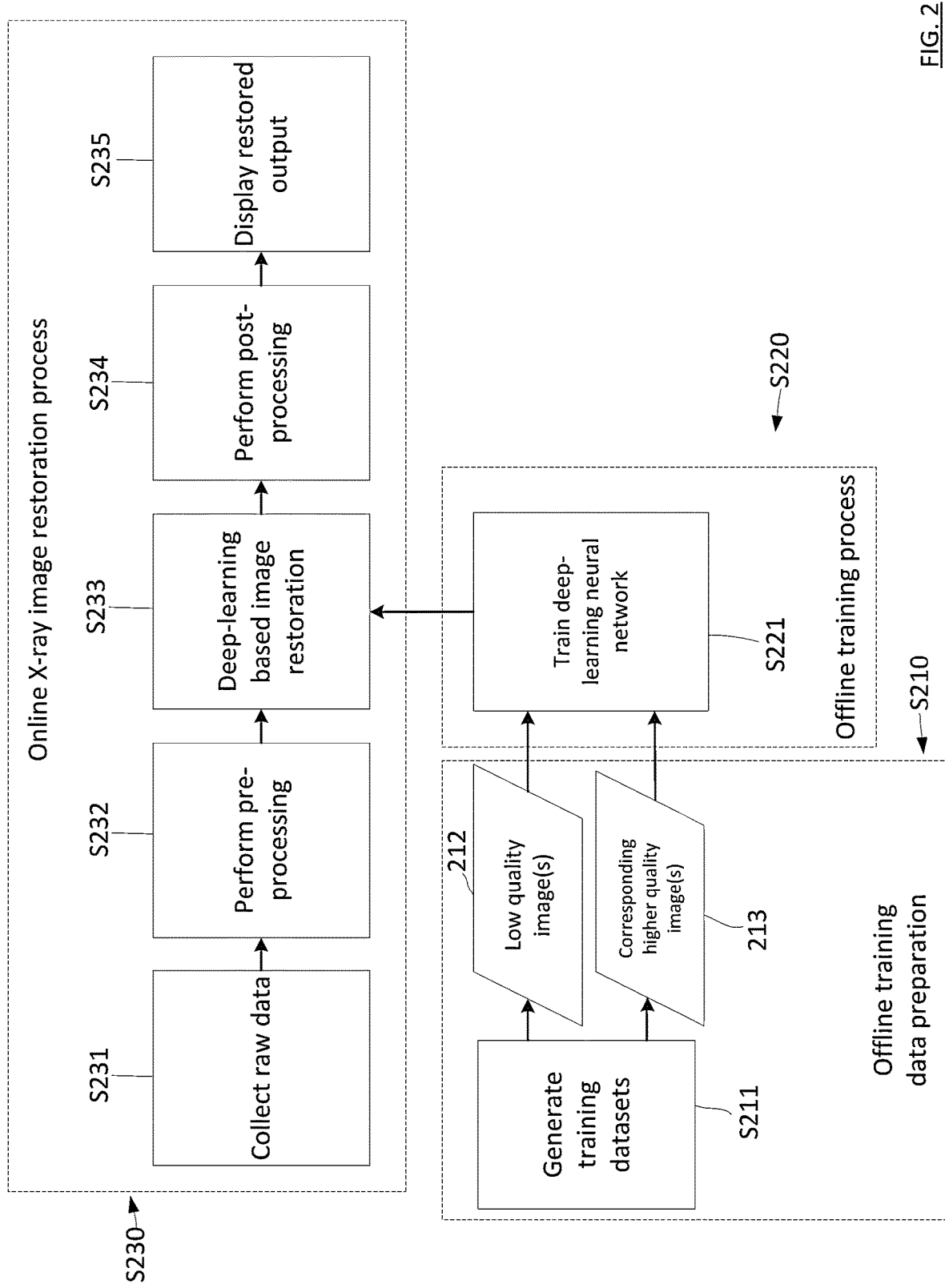
FIG. 2 is workflow diagram for imaging restoration using deep learning algorithms, according to one exemplary embodiment of the present disclosure.

FIG. 2 illustrates a general workflow according to one exemplary embodiment, which includes offline training data preparation S210, an offline training process S220, and online X-ray image restoration S230. The workflow begins with offline training data preparation S210. Step S210 includes generating (S211) training datasets to produce one or more lower quality images 212 corresponding to a number of higher quality images 213. Each lower quality image 212 has more noise and blur than its corresponding higher quality image 213. These lower quality images 212 and higher quality images 213 can then be used as training data to train the deep-learning neural network S211 in the offline training process S220, using the lower quality images 212 as an input and their corresponding higher quality images 213 as the target output, thereby producing a trained deep-learning neural network. The training can include updating weights in the deep-learning neural network to map the input to the target output.

The trained deep-learning neural network produced upon completion of the offline training process S220 can then be used for real-time, online X-ray image restoration S230. This process begins with the step of collecting raw data S231, such as X-ray data from a scan of the object OBJ. This raw data is then pre-processed in S232 to create an initial image. This initial, full size image can then be snipped (i.e., segmented or cropped) to create image patch snippets making up the full sized image. The image patch snippets are then input into one or more deep-learning neural networks trained during S221 to perform deep-learning based image restoration S233, which outputs a higher quality version of the input image. The improvement in quality can be in the form of less blur or noise. The image is then post-processed S234. For example, if image patch snippets were created, they can be put back together to form a whole, full size image. Upon performing post-processing S234, the restored output can be displayed S235 to a user.

Additional details of the general workflow of FIG. 2 will be discussed with reference to additional figures. FIGS. 3A, 3B, 4A, and 4B will be used to facilitate a discussion on generating training datasets and training the deep-learning neural networks, and FIG. 5 will be used to facilitate a discussion on utilizing the trained deep-learning neural network for real-time image restoration.

Figure 3A:
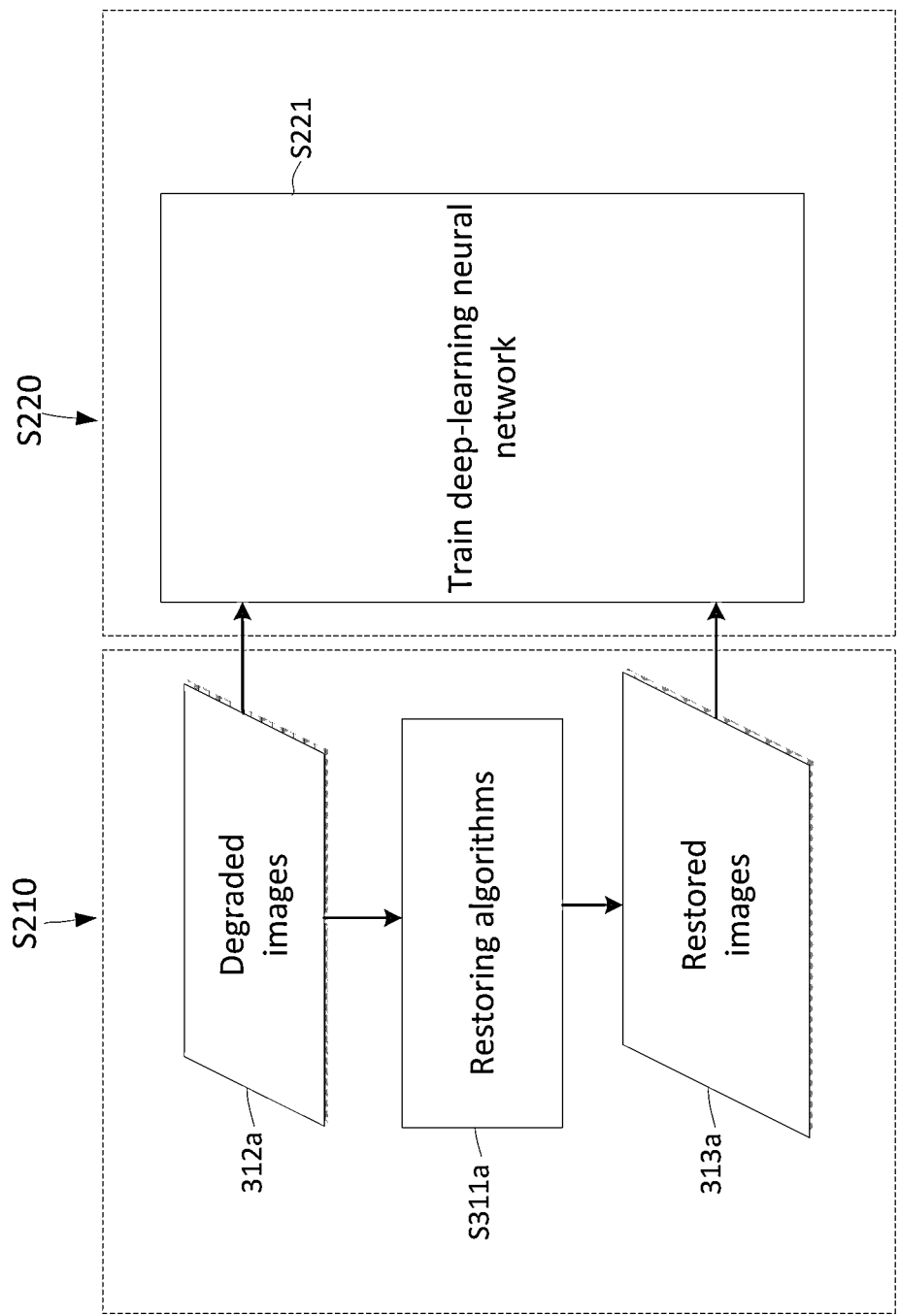
FIG. 3A is a workflow diagram for training data preparation, according to one exemplary embodiment of the present disclosure.

FIG. 3A shows one exemplary embodiment for offline training data preparation S210. In this example, dataset generation starts off by gathering lower quality images 212, referred to in FIG. 3A as degraded images 312a, such as degraded clinical images of a patient. Then, in S311a, one or more restoring algorithms are applied to the degraded images 312a. The restoring algorithms used in S311a can deblur and/or denoise the degraded images 312a to produce higher quality images 213, referred to in FIG. 3A as restored images 313a. Examples of restoring algorithms that can be used as the restoring algorithms S311a include, but are not limited to, semi- or un-supervised deep learning methods, non-local means methods, and Markov random field-based methods. Note that even though these restoring algorithms can be used to deblur and/or denoise images to some extent, they are often computationally consuming and inconsistent in producing high quality results compared to the techniques discussed herein. These degraded images 312a and their corresponding restored images 313a can then be used for training the deep-learning neural network S221 in the offline training process S220.

Figure 3B:
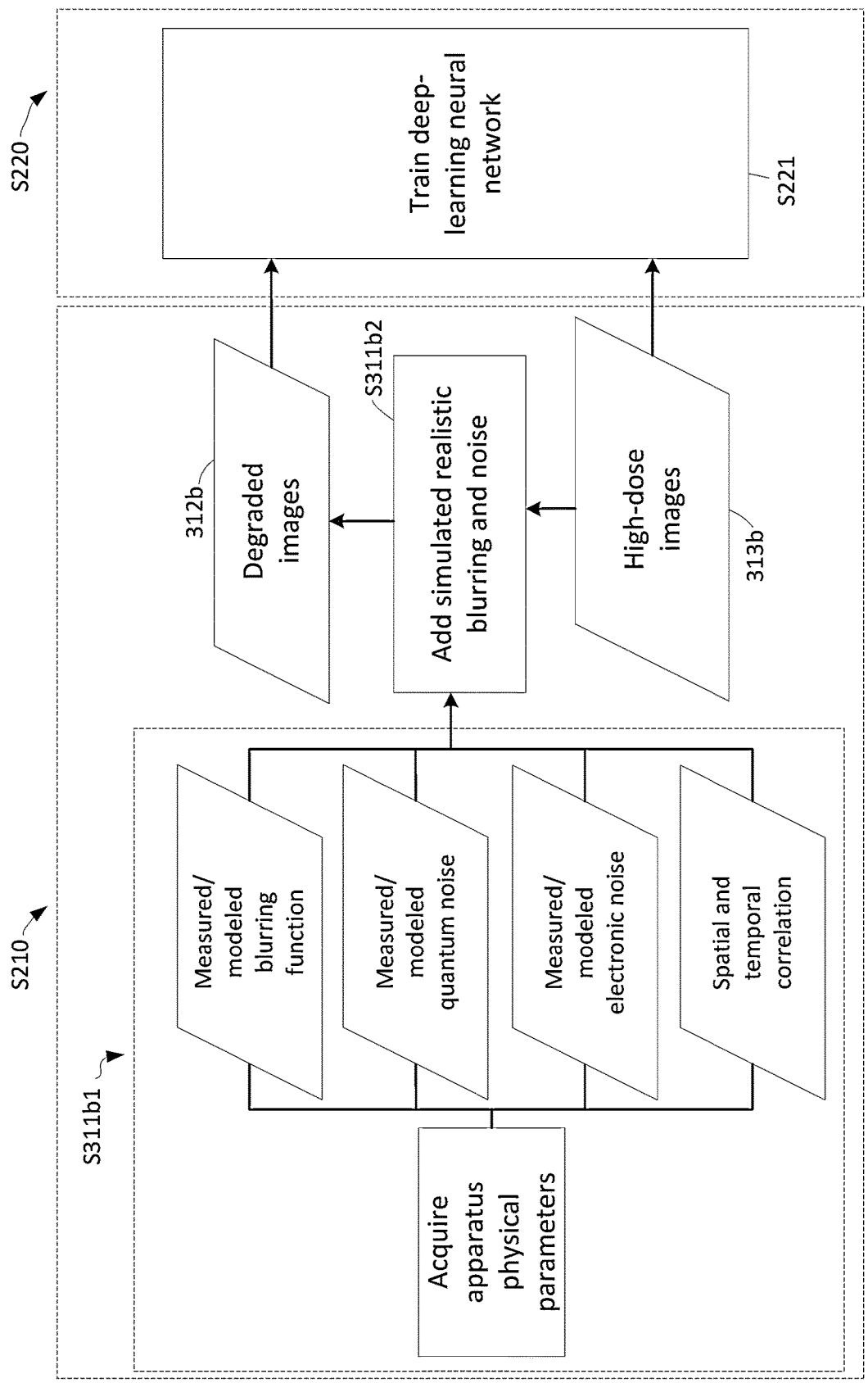
FIG. 3B is a workflow diagram for training data preparation, according to one exemplary embodiment of the present disclosure.

FIG. 3B shows another exemplary embodiment for offline training data preparation S210. In this example, dataset generation starts off by gathering higher quality images 213, such as high-dose images 313b of one or more patients. Then, simulated realistic blurring and/or noise is added in S311b2 to the high-dose images 313b to produced lower quality images 212, referred to in FIG. 3B as degraded images 312b. These degraded images 312b and their corresponding high-dose images 313b can then be used for training the deep-learning neural network S221 in the offline training process S220.

Because different physical parameters in the apparatus can generate different blurring functions and noise properties (e.g. an X-ray system will have different noise, blurring, and correlation factors than a PET scanner system), they can be considered separately during S311b1 when determining the simulated realistic blurring and noise to be added during S311b2. S311b1 comprises acquiring physical parameters of the apparatus.

During S311b1, a variety of apparatus physical parameters can be incorporated, such as: measured or modelled blurring functions, measured or modelled quantum noise, measured or modelled electronic noise, spatial and temporal correlation, or any combination thereof. In one embodiment, a measured or modelled blurring function can add realistic blurring caused from various factors such as light spreading caused by the scintillator, a finite focal spot size, patient motion, or detector binning. Realistic noise can include quantum noise and electronic noise. Furthermore, the spatial and temporal correlation from both quantum noise and electronic noise can be measured or modelled. It should be understood that the above-mentioned techniques are just a few of many ways that high quality images can be degraded to create lower quality images. Accordingly, it can be appreciated that many other techniques can be used for accomplishing the overall purpose of this step.

Figure 4A:
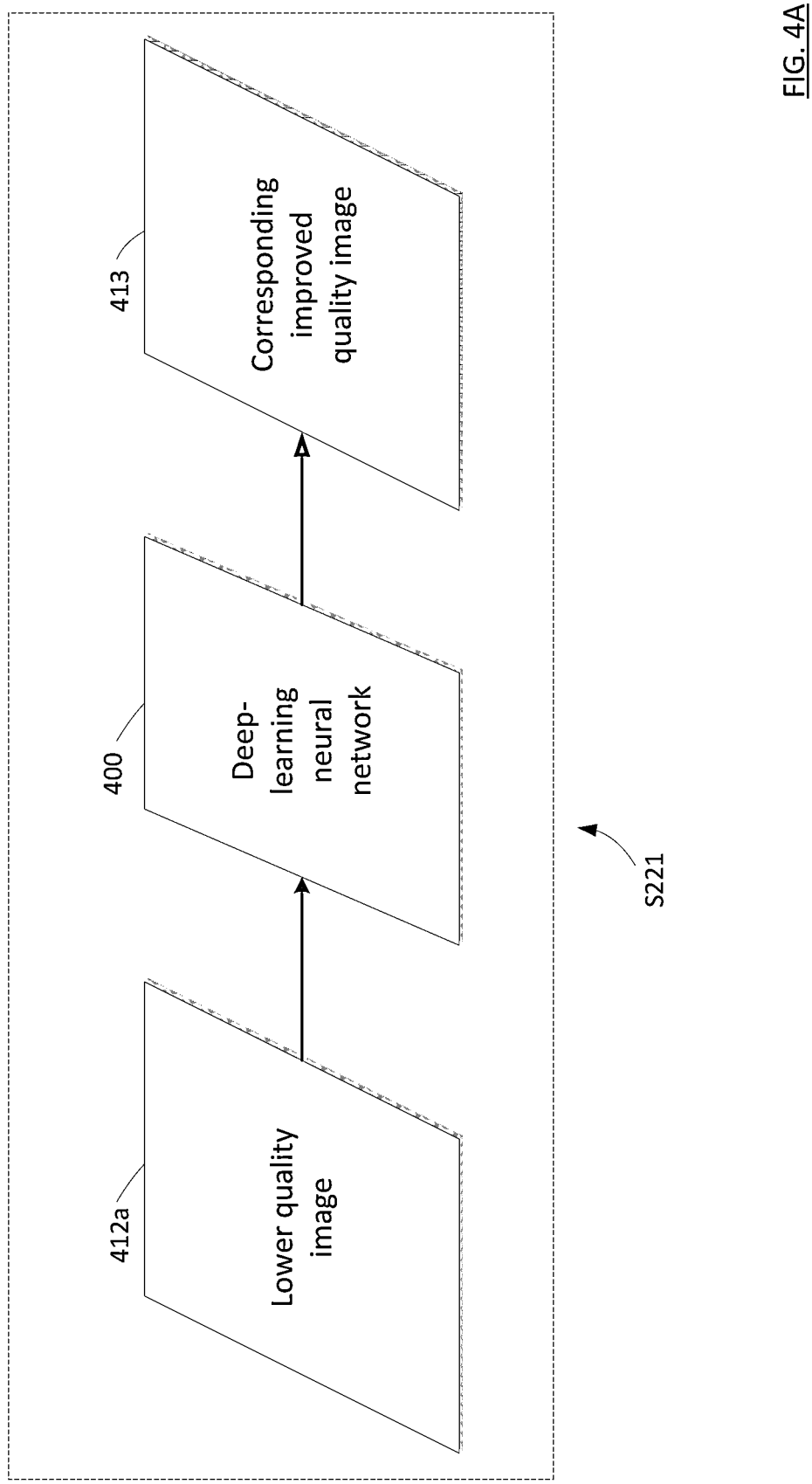
FIG. 4A is a workflow diagram of a training process, according to one exemplary embodiment of the present disclosure.

FIG. 4A shows one embodiment for training the deep-learning neural network S221. A single lower quality image 412a is the input learning data, and a single corresponding improved quality image 413 is the output learning data. The deep-learning neural network 400 can be trained to find a set of weights that optimally map the lower quality image 412a to its corresponding improved quality image 413. In one embodiment, the loss function for the deep-learning neural network 400 can be designed to minimize the noise-weighted difference between the lower quality image 412a (input) and the corresponding improved quality image 413 (target). In one embodiment, the loss function can be a mean squared error/mean absolute error between the inferenced and target images. Additionally, a mask may be applied to focus on the specific parts of interest. Multiple lower quality images 412a and their corresponding high quality images 413 can be used for training the deep-learning neural network 400 until it is able to consistently produce acceptable higher quality images.

Figure 4B:
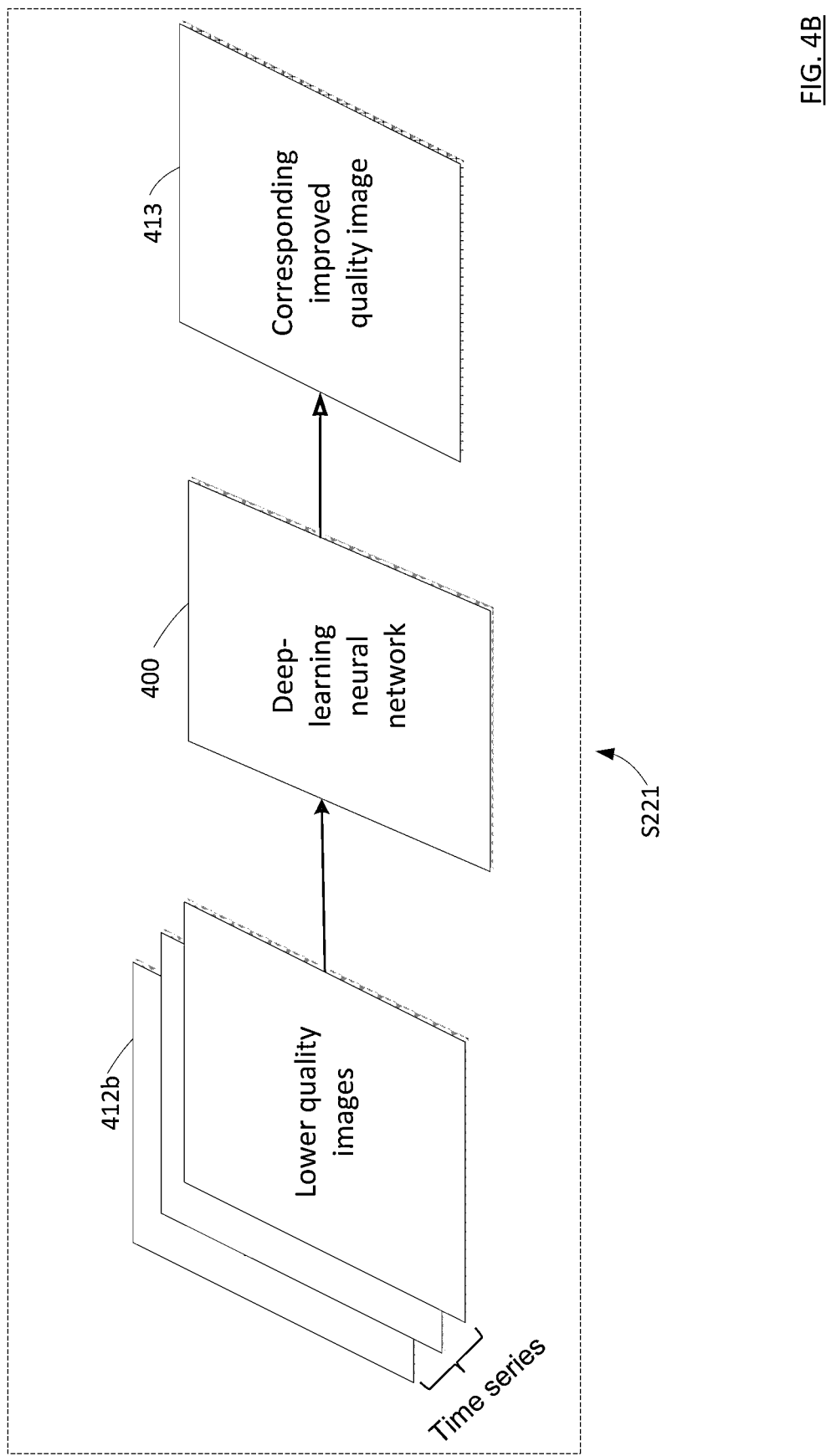
FIG. 4B is a workflow diagram of a training process, according to one exemplary embodiment of the present disclosure.

FIG. 4B shows another embodiment for the training the deep-learning neural network S221. Time series lower quality images 412b can contain more information than a single lower quality image 412a, such as history information of how elements in the images have transformed over time. Thus, in another exemplary embodiment, a time series of lower quality images 412b generated during the offline training data preparation S210 can be input learning data for the deep-learning neural network 400, and a single corresponding improved quality image 413 can be the target output. Temporal information can be used to reduce flickering. The loss function for the deep-learning neural network 400 can be designed to minimize the noise-weighted difference between the time series of lower quality images 412b (input) and a corresponding improved quality image 413 (target), as well as the noise-weighted difference between adjacent frames of the time series of lower quality images 412b. For example, the loss function could be a mean squared error/mean absolute error between the inferenced and target images, as well as a mean squared error/mean absolute error between one or more previous frames and a current frame in the time series of images. Additionally, a mask may be applied to focus on specific parts of interest. This process can be repeated until the deep-learning neural network 400 is sufficiently trained to produce acceptable higher quality images.

FIG. 5 illustrates one exemplary embodiment for performing the online X-ray image restoration S230. After generating training datasets S211 during offline training data preparation S210 to produce high/low image pairs 212, 213, they can be used to train the deep-learning neural network 400 in the offline training process S220. This deep-learning neural network 400 can then be optimized (e.g. pruning, precision reduction) and used in the online X-ray image restoration process S230.

The online X-ray image restoration process S230 begins with collecting raw data S231. This raw data can be the data gathered by an imaging system for constructing an image. For example, the raw data can include the X-ray transmitted through the object OBJ and detected by the two-dimensional array of detection elements in the detection system 114.

The next step is performing pre-processing S232, which can be performed by one or more pre-processing circuitry 121 units. The pre-processing circuitry 121 can be configured to execute sensitivity correction, suppress distortions, or transform the raw data collected by the detection system 114 to a full size image 532. In one embodiment, this full size image 532 can be further divided into snippets of image patches, IP1 through IPN, where N is the total number patches. Dividing the full size image 532 into image patches can enable more efficient processing. The full size image 532 can be divided in many different ways. For example, the full size image 532 can be divided into equal size regions, such as into quadrants or octants. As another example, the full size image 532 can be divided so that each image patch is a particular anatomical structure, such as a hand, chest, foot, leg, or skull. As another example, the full size image 532 can be divided so that each image patch is a subset of one or more slices. Additionally, neighboring image patches can have overlap at their borders, which can ease reassembling the image patches back into a full size image later on in the process. Next, these image patches IP1 to IPN can be used for deep learning based image restoration S233. As can be appreciated, the full size image 532 does not always have to be divided into snippets image patches (i.e. the full size image 532 can be used in S233).

The next step is to perform deep learning based image restoration S233. In one embodiment, this can be performed by the image processing circuitry 122. In one embodiment, after the deep-learning neural network 400 has been trained, it can optimized through pruning S501 and having its precision reduced S502 prior to being configured into one or more image restoration processors IRPs. Performing pruning S501 can involve removing parameters from the deep-learning neural network 400 to reduce its size. S501 can include removing unnecessary weights in the deep-learning neural network 400 and may be performed iteratively. Performing precision reduction S502 can involve reducing the number of bits used in the deep-learning neural network 400, which can allow for faster arithmetic. For example, if the deep-learning neural network 400 was trained using 64-bits during the offline training process S220, S502 can decrease the bits used in computing to 32-bits, 16-bits, 8-bits, etc.

Figure 6A:
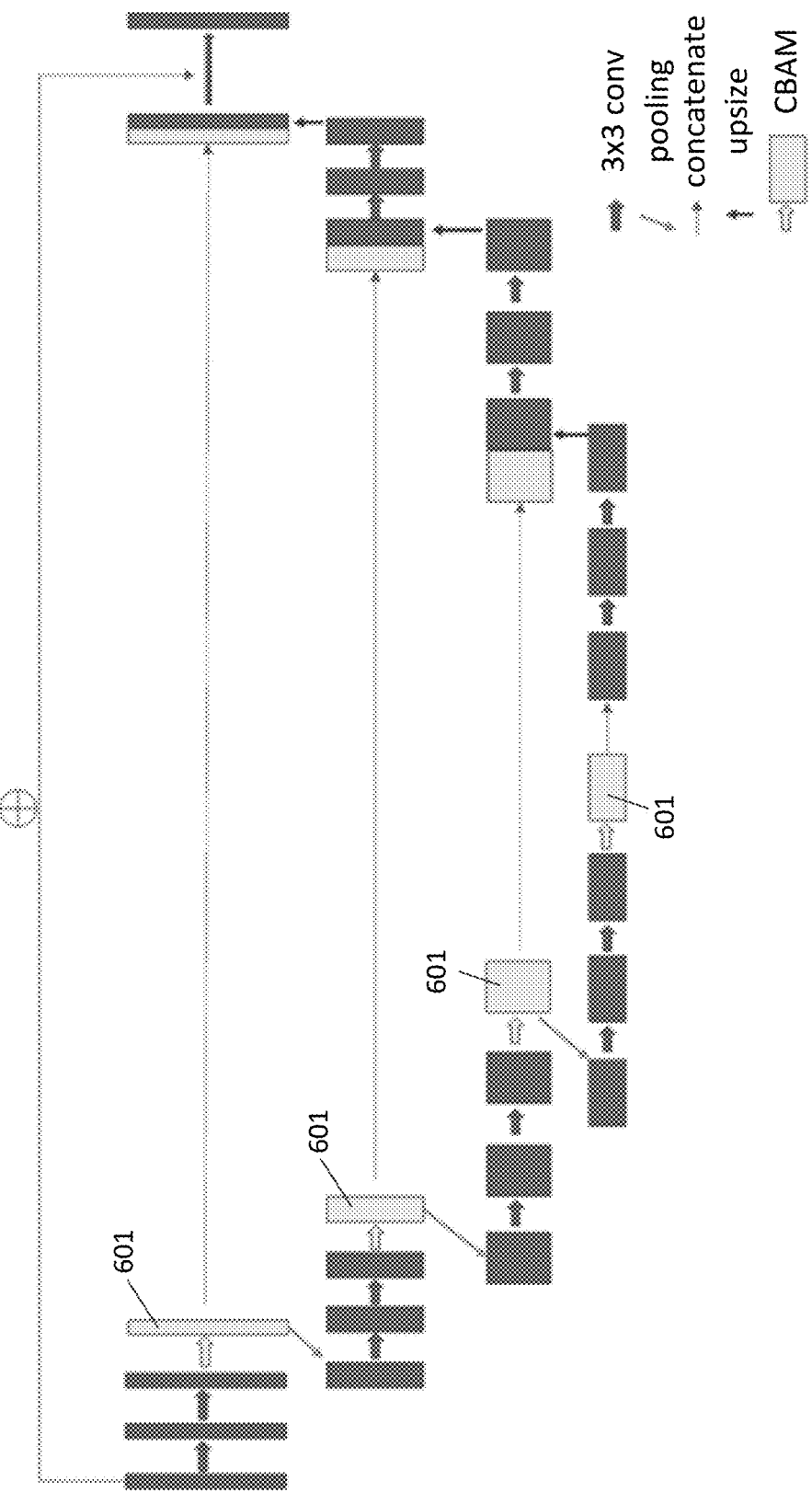
FIG. 6A illustrates a convolutional block attention module (CBAM) attached onto a U-net, according to one exemplary embodiment of the present disclosure.
Figure 6B:
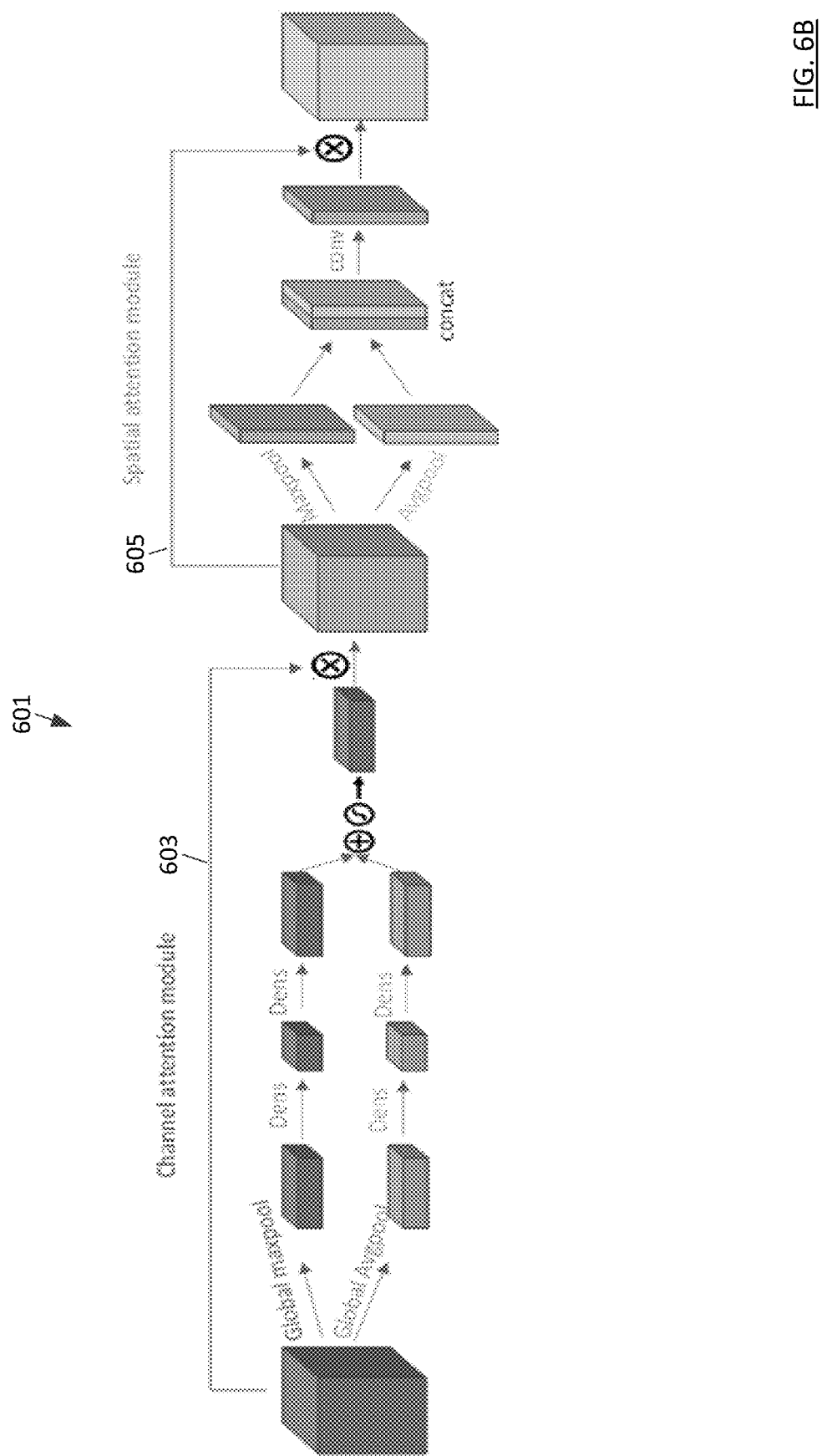
FIG. 6B illustrates an architecture of a CBAM, according to one exemplary embodiment of the present disclosure.

In an embodiment, a convolutional block attention module (CBAM) can be added to the deep-learning neural network 400. FIG. 6A illustrates an exemplary embodiment, where a CBAM 601 is attached to a U-net convolutional neural network right before concatenation. FIG. 6B shows an example of a CBAM 601, which include a channel attention module 603 and a spatial attention module 605. In an embodiment, the CBAM can have either or both of the channel attention module 603 and a spatial attention module 605, and in either order. In an embodiment, the CBAM can have light, trainable weights so that it can be flexibly attached to any neural network. The use of the CBAM can improve denoising and restoration performance of the deep-learning neural network 400.

After the deep-learning neural network 400 has been optimized, it can be configured into one or more image restoration processors IRPs, which can be housed in the image processing circuitry 122. Multiple image restoration processors IRPs can be used in series or parallel to speed up the inferencing process. For example, N image restoration processors can be configured in parallel to restore the N image patches. Each of the image patches IP1-IPN can be input into an image restoration processor IRP for outputting a higher quality version (e.g. less blur, less noise) of the input image patch IP1-IPN (or full size image 532). The use of multiple processors can accelerate the online inferencing process. Next, these higher quality image patch IP1-IPN outputs can be collected and combined during post-processing S234 to create a transformed, higher quality full size image. S234 can be performed by the image-processing circuitry 122. (Similarly, parallel architectures (such as single instruction, multiple data architectures) can be used for enhanced performance.) In displaying the restored output S235, this higher quality full size image can displayed using the display 123.

In one embodiment, during the training data preparation S210 and training process S220, an anatomic structure-based training strategy can be used to fully capture the image features at different anatomic structures and optimize the image quality. Training datasets can be classified based on anatomical structures. Multiple deep-learning neural networks 400 can be trained based on different training datasets. For example, a first deep-learning neural network 400 can be trained using high and low image pairs of a hand, while a second deep-learning neural network 400 can be trained using high and low image pairs of a skull. During S230, the first deep-learning neural network 400 can be configured into a first image restoration processor IRP1 for receiving image patches of hands, while the second deep-learning neural network 400 can be configured into a second image restoration processor IRP2 for receiving image patches of skulls. Similarly, the training pairs can be used to train a network along with information on (a) the conditions under which the lower quality image was obtained or (b) the simulated conditions under which it was generated to appear to have been obtained. In doing so, the neural network may be trained to correct noise and blur under image-specific conditions.

Figure 7:
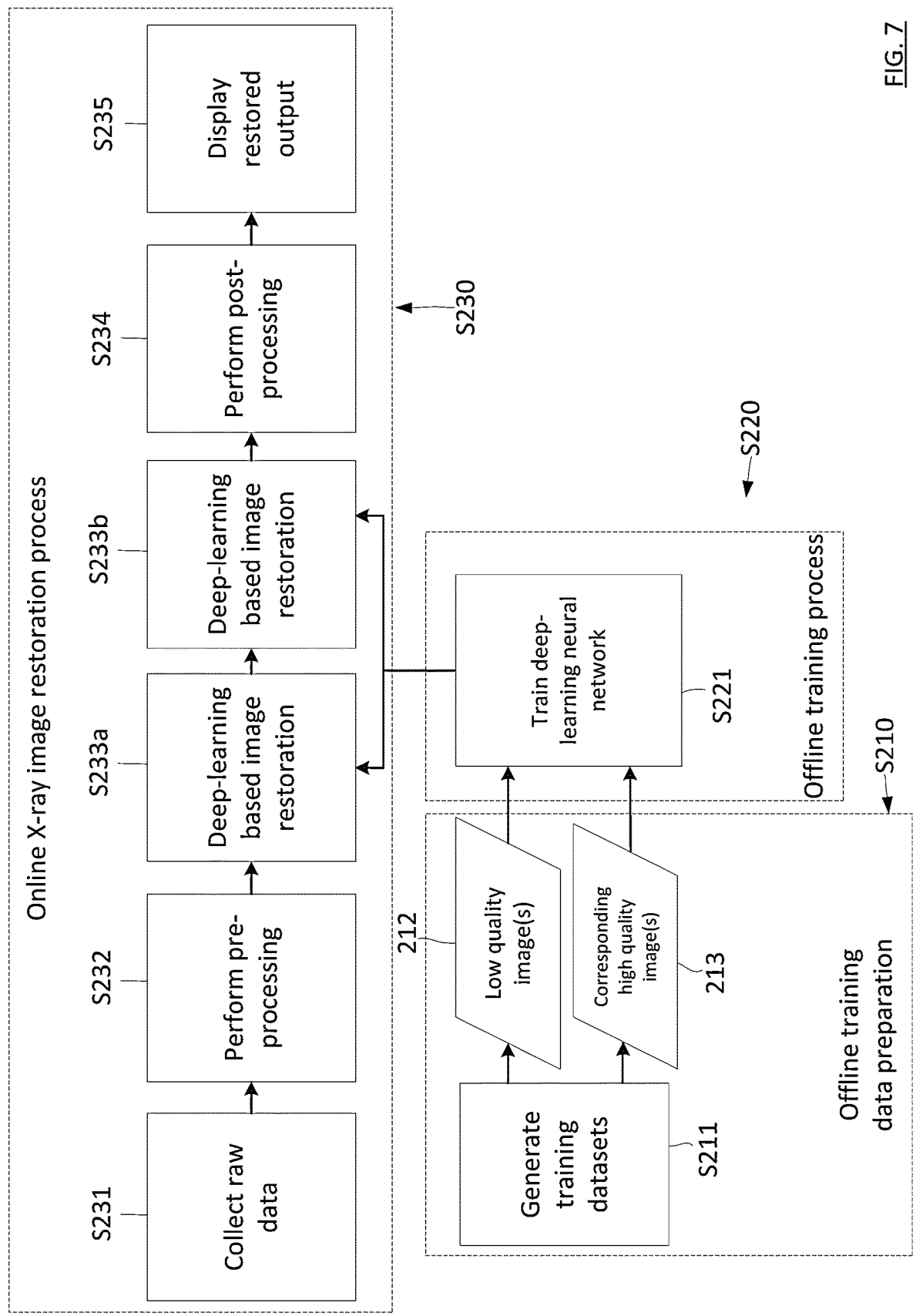
FIG. 7 is a workflow diagram of an X-ray image restoration process, according to one exemplary embodiment of the present disclosure.

In another embodiment, steps such as performing pre-processing S232, deep-learning based image restoration S233, and performing post-processing S234 can be chained together in series or in parallel and performed multiple times. For example, as illustrated in FIG. 7, a first deep-learning based image restoration step S233*a* can occur for removing noise using a first deep-learning neural network trained in S221 for removing noise, followed by a second deep-learning based image restoration step S233*b* using a second deep-learning neural network trained in S221 for removing blur. As another example, after performing a first series of pre-processing S232, deep-learning based image restoration S233, and post-processing S234, where the pre-processing S232 used image patches that were divided into quadrants, a second round of pre-processing S232, deep-learning based image restoration S233, and post-processing S234 can be performed where the image patches are divided using a different technique, such as into one or more slices or specific anatomical parts.

In one embodiment, the training data preparation S210 and training process S220 can be implemented as software. A computer processor having embedded memory can store computer instructions for performing the processes described herein. In another embodiment, the training data preparation S210 and training process S220 can be implemented as hardware. The processes described above can be implemented in processing circuitry, such as an application specific integrated circuit (ASIC) or a field programmable gate array (FPGA). The FPGA may be programmed as a trained neural network at hardware startup, or the FPGA may be reprogrammed as a new, special purpose neural network each time the usage conditions change (e.g., when changing from a hand-specific neural network to a skull-specific neural network, or when changing from an image taken at a first radiation dose or expose to a second radiation dose or exposure).

Figure 8:
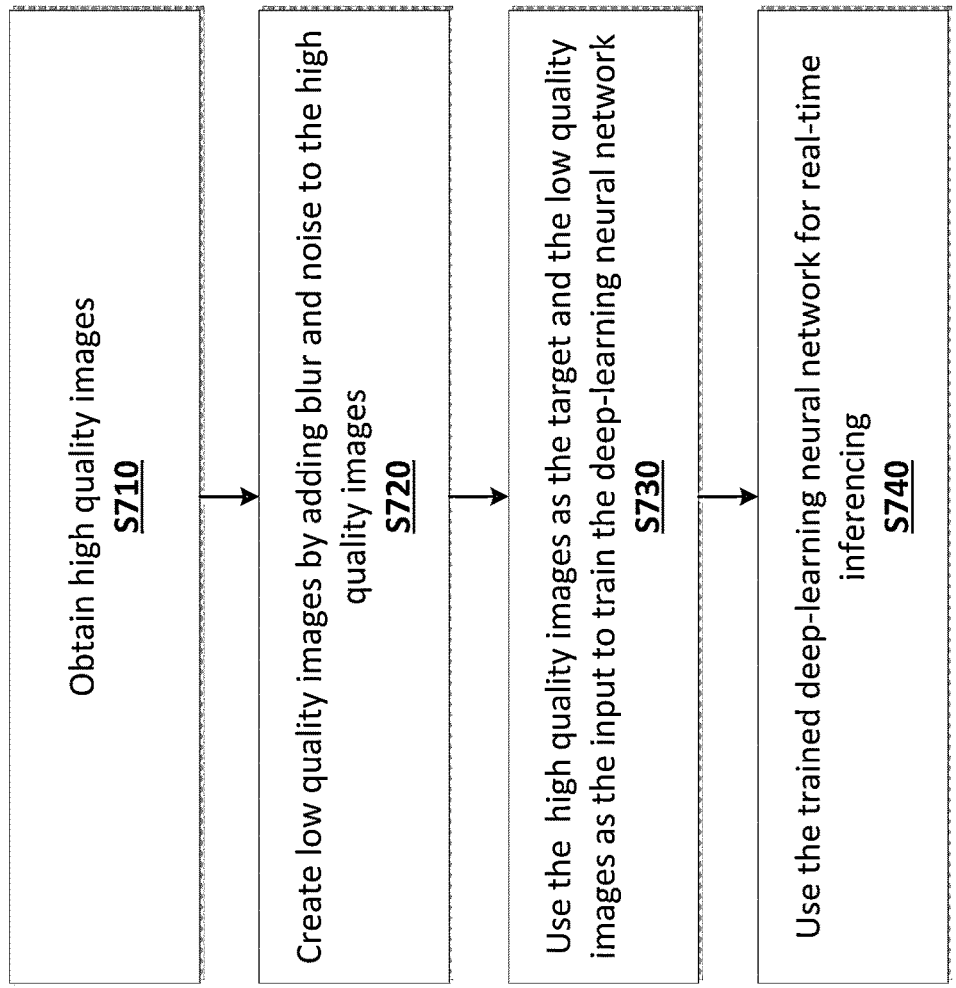
FIG. 8 is a method for training a deep-learning neural network, according to one exemplary embodiment of the present disclosure.

It can be appreciated that the above mentioned techniques can be implemented as a method. One method 700 for training and utilizing a deep-learning neural network for image restoration is illustrated in FIG. 8. The first step S710 is to obtain one or more high quality images. These images can be high quality clinical images of patients. The next step S720 is to create one or more lower quality images by adding blur and noise to the high quality images obtained in S710. The noise and blur to be added can be dependent on parameters of the apparatus used to obtain the high quality images. Examples of factors that can be considered include measured or modelled blurring, measured or modelled quantum noise, measured or modelled electronic noise, and spatial and temporal correlation. The goal is to create one or more images that have more blur and noise than the high quality images. The next step S730 is to train a deep-learning neural network by using the high quality images as the output target and the low quality images as the input. Once the deep-learning neural network has been trained, the trained deep-learning neural network can be pruned and precision reduced for use in real-time inferencing S740.

Figure 9:
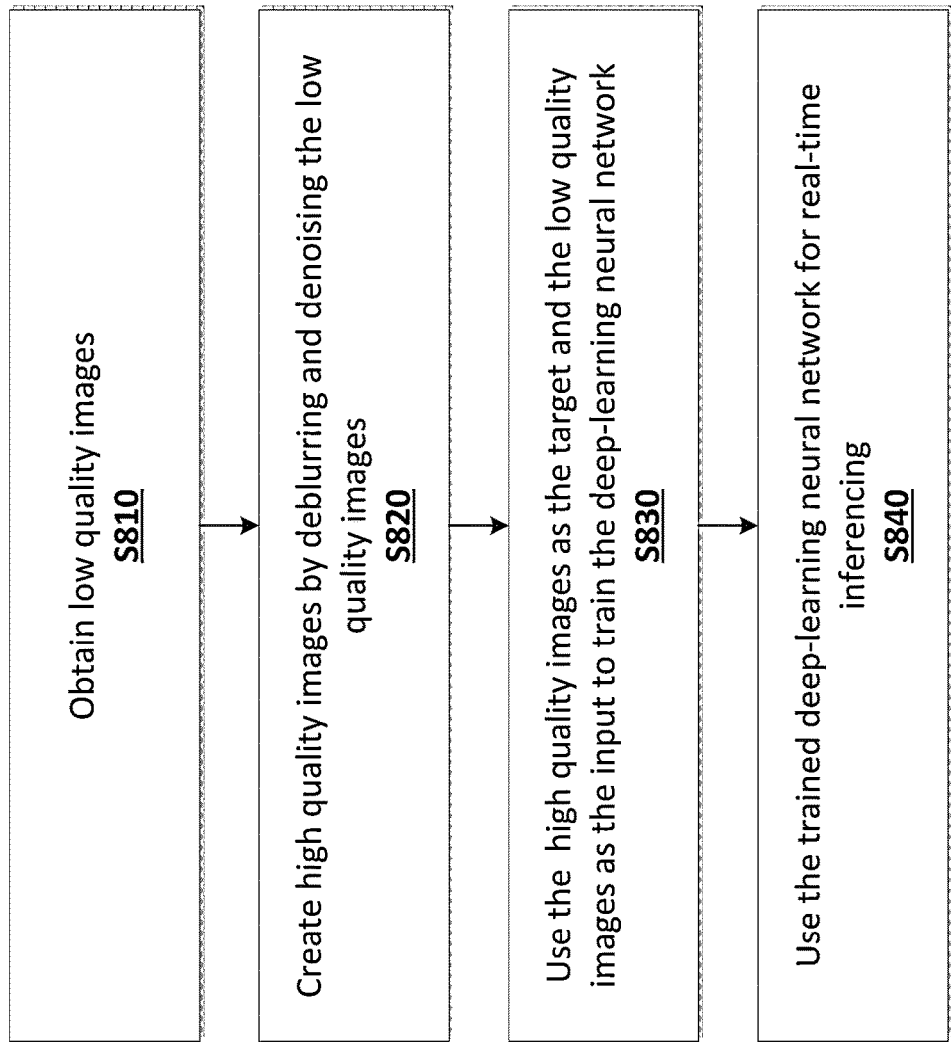
FIG. 9 is a method for training a deep-learning neural network, according to one exemplary embodiment of the present disclosure.

Another method 800 for training and utilizing a deep-learning neural network for image restoration is illustrated in FIG. 9 using a flowchart. The first step S810 is to obtain one or more low quality images S810, such as noisy or blurry clinical X-ray images of patients. The next step S820 is to create high quality images by deblurring and denoising the lower quality images obtained in S810. Algorithms that can be used to remove blur and noise, include, but are not limited to, semi- or un-supervised deep learning methods, non-local means methods, and Markov random field-based methods. The goal is to create higher quality images with less blur and noise than the low quality images obtained in S810. The next step 830 is to train a deep-learning neural network by using the higher quality images as the output target and the low quality images as the input. Once the deep-learning neural network has been trained, the trained deep-learning neural network can be pruned and precision reduced used for real-time inferencing S840.

In both S730 of FIG. 8 and S830 of FIG. 9, the input into the deep-learning neural network can be a single frame and a loss function can be designed to minimize the noise-weighted difference between the input and the target output. In another exemplary embodiment, the input can be multiple frames, and the loss function can be designed to minimize the noise-weighted difference between the multi-frame inputs and the target output, as well as the noise-weighted difference between adjacent frames.

Figure 10:
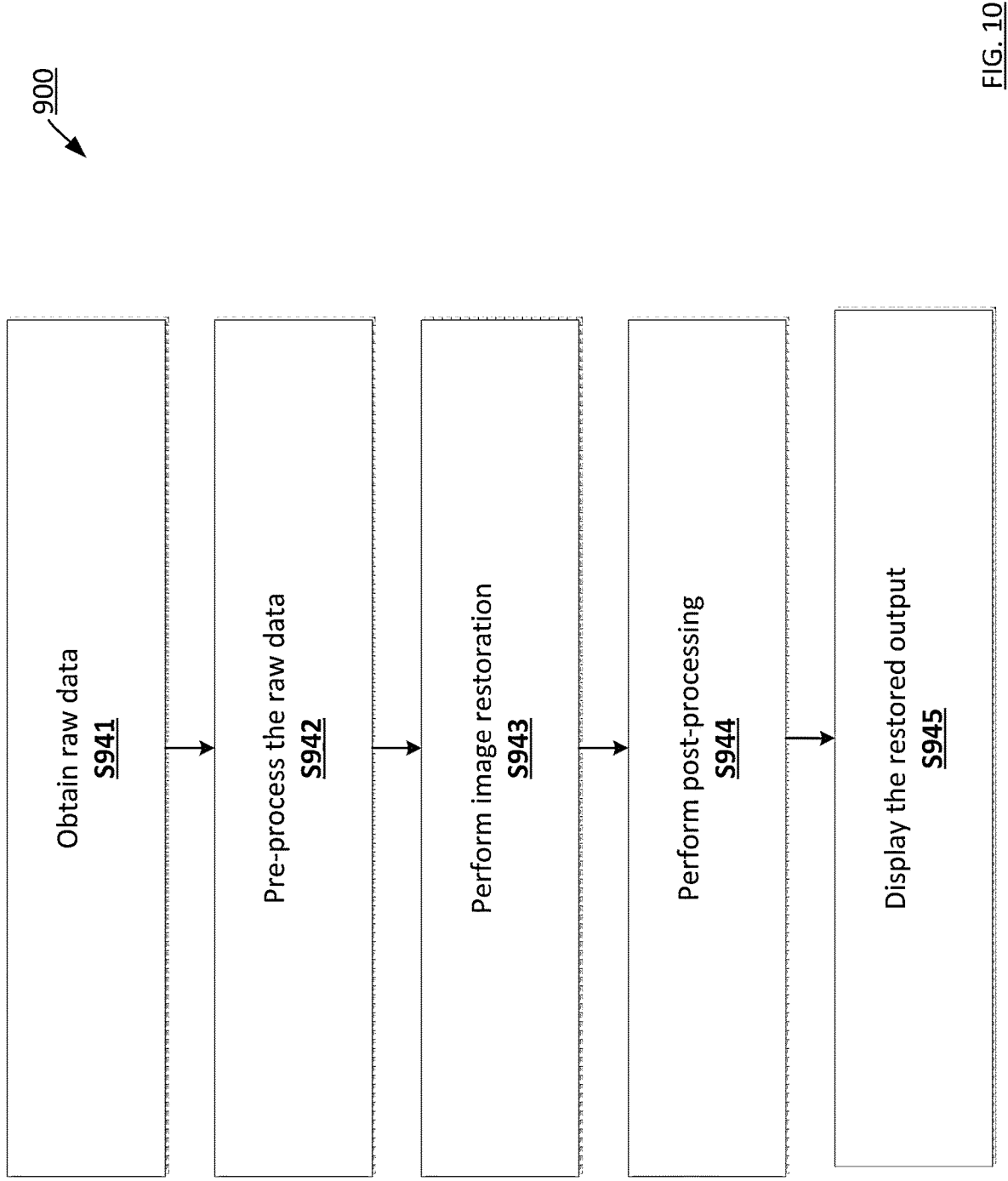
FIG. 10 is a method for obtaining an image with less blur and noise using a trained deep-learning neural network.

Additional details of how to use the trained deep-learning neural network produced according method 700 and 800 for real-time inferencing are illustrated in FIG. 10. The method 900 starts with obtaining raw data S941. Obtaining raw data can include collecting information from scanning a patient during an X-ray. The next step S942 is to pre-process the raw data. Pre-processing the raw data can include using the raw data to create a full size image. Further, this image can be divided into snippets of image patches. The next step S943 is to perform image reconstruction S943. The full size image or image patches generated from S942 can be input into the trained deep-learning neural network. As it was trained to do, the deep-learning neural network can then output higher quality images of the input, wherein the higher quality images have reduced blur and noise. The next step S944 is to perform post-processing, which can include putting the new and improved image together. If pre-processing the raw data S942 involved creating image patches, the post-processing S944 can put the newly generated image patches back together to form a full size image. Lastly, the restored output can be displayed S945.

Figure 11:
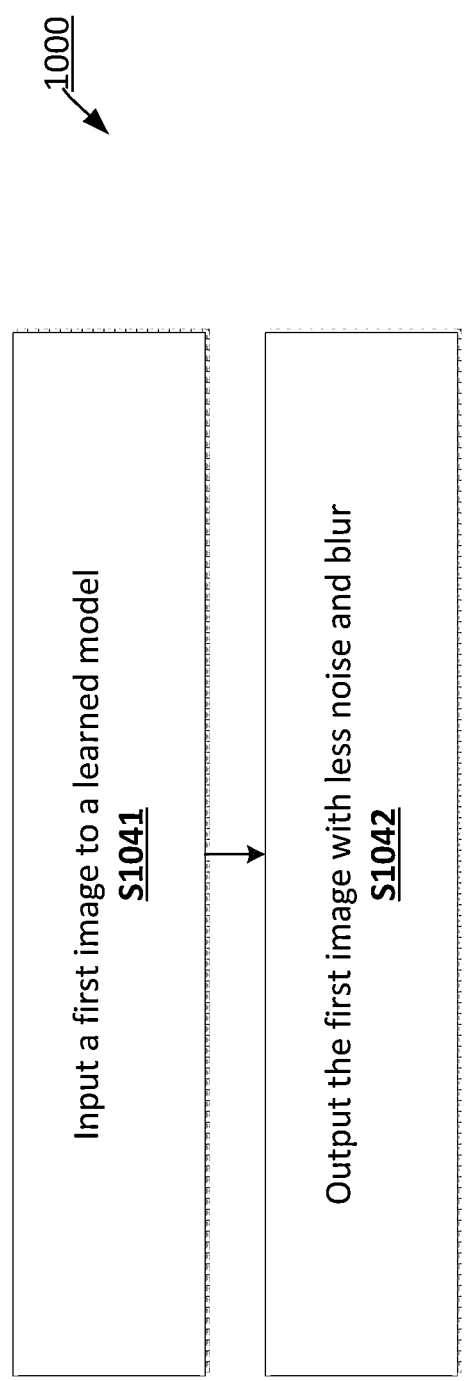
FIG. 11 is a method for obtaining an image with less blur and noise using a trained deep-learning neural network.

FIG. 11 illustrates another exemplary embodiment of a method 1000 for using the trained deep-learning neural network for real-time image restoration. In S1041, a first image is input to a learned model, where the learned model can be the trained deep-learning neural network produced according to method 700 or 800. The first image can be made with raw data obtained during an X-ray scan of a patient. Next, in S1042, the first image is output from the learned model with less noise and blur than when it was input in S1041.

Figure 12:
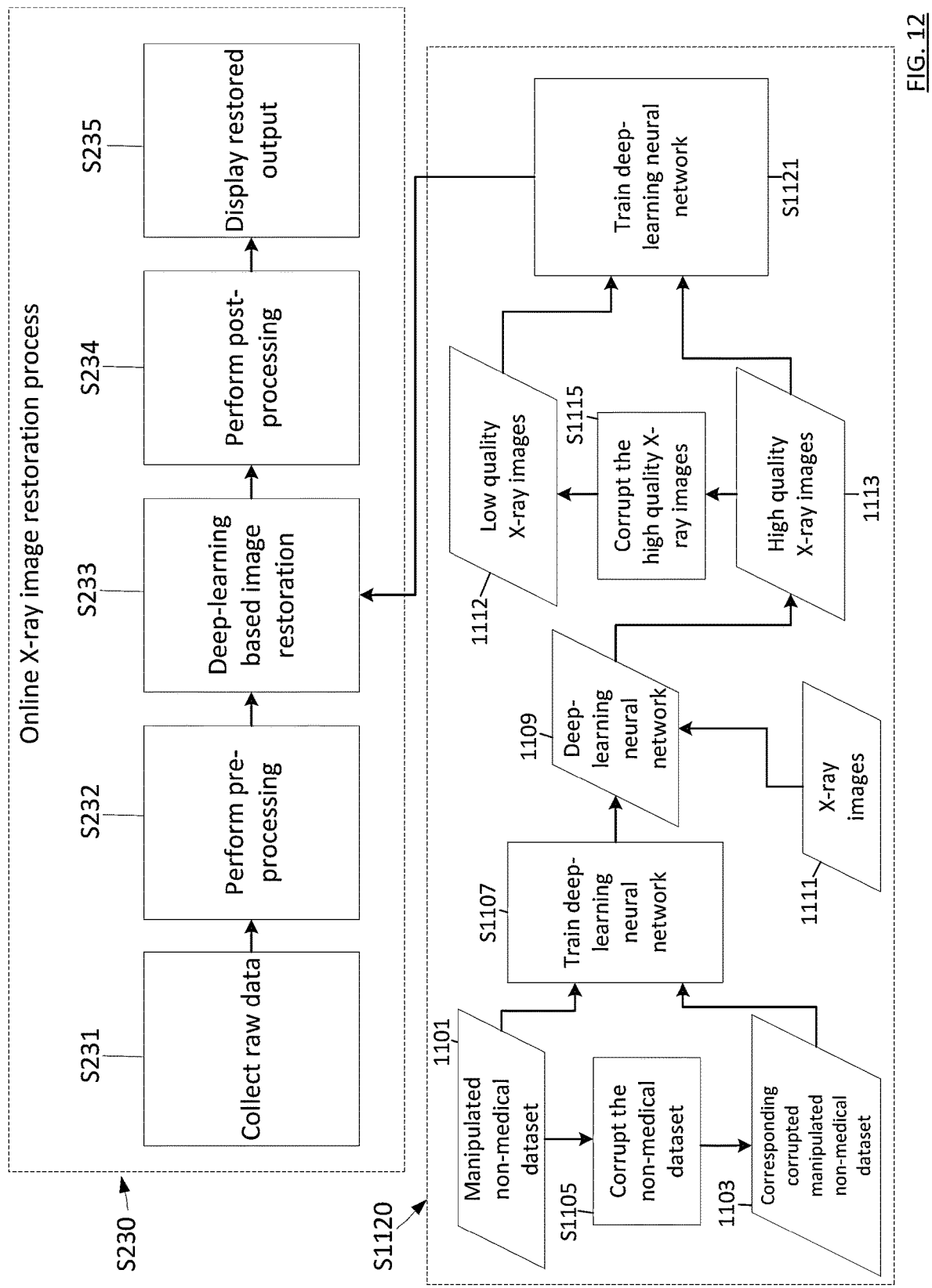
FIG. 12 is a workflow diagram illustrating the use of manipulated non-medical datasets to generate high quality X-ray images for training a neural network for online X-ray image restoration.

FIG. 12 illustrates a workflow for one embodiment of dataset generation that can be used in training. During offline dataset generation in S1120, a manipulated non-medical dataset 1101 is first obtained. This manipulated non-medical dataset 1101 does not need to be an actual medical image (e.g. patient scan), thereby encompassing a wide range of possible datasets that can be used. In this context, manipulation refers to transforming a non-medical dataset to resemble an X-ray dataset using any technique known by one of skill in the art. In other words, a non-medical dataset is manipulated to resemble an X-ray dataset, thereby forming the manipulated non-medical dataset 1101.

In S1105, the manipulated non-medical dataset 1101 is corrupted to generate a corresponding corrupted manipulated non-medical dataset 1103. Various forms of corruption can be included, such as adding noise or blur. In one embodiment, the techniques described with respect step S311b2 in FIG. 3B can be applied.

In S1107, a deep learning neural network is trained using the manipulated non-medical dataset 1101 as output learning data, and the corresponding corrupted manipulated non-medical dataset 1103 as input learning data. The training can be performed until a predetermined stopping criteria has been met. The outcome of S1107 is deep-learning neural network 1109.

The deep-learning neural network 1109 can now take as input X-ray images 1111, which are medical images, and generate high quality X-ray images 1113. In S1115, the high quality X-ray images 1113 are corrupted to produce corresponding low quality X-ray images 1112. In one embodiment, the same corruption technique as described in S311b2 of FIG. 3B can be applied.

S1121 is to train a deep-learning neural network using the high quality X-ray images 1113 as output training data, and the low quality X-ray images 1112 as input training data. Once S1121 has been completed, the trained neural network can be used for deep-learning based image restoration, as previously described in S233.

In another embodiment related to the workflow discussed with reference to FIG. 12, metadata can be incorporated, such as a patient's condition (e.g. patient's body mass index) or a description of an image (e.g. procedure that generated the image). For example, the deep-learning neural network trained in S1121 can use low quality X-ray images 1112 (input training data), high quality X-ray images 113 (output training data), and metadata (input training data) during training. Furthermore, metadata can be used to further corrupt the low quality X-ray images 1112. For example, for a patient with a high body mass index, a different kernel that can simulate more realistic images can be used to corrupt the low quality X-ray images 1112. Lastly, the metadata can be an additional input in the deep-learning based image restoration of S233.

Figure 13:
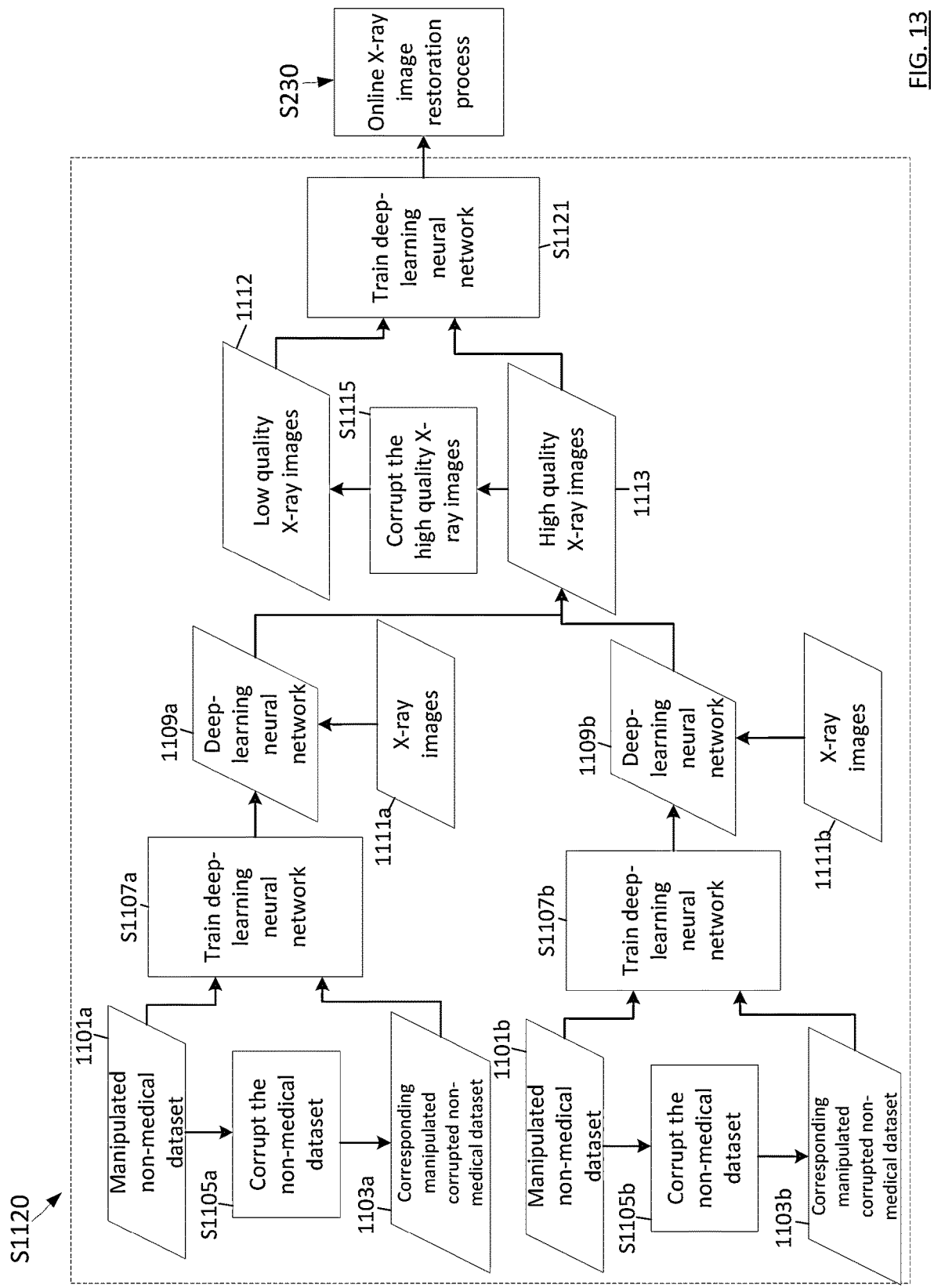
FIG. 13 is a workflow diagram illustrating the use of multiple types of manipulated non-medical datasets to generate multiple types of high quality X-ray images for training a neural network for online X-ray image restoration.

FIG. 13 illustrates another workflow for offline data generation in S1120 similar to the workflow discussed in FIG. 12. In this case, multiple neural networks can be trained to take X-ray images of multiple types.

First, manipulated non-medical dataset 1101a and manipulated non-medical dataset 1101b are obtained. These two datasets can differ in that they have different features and resemble different types of 2-D X-ray scan datasets. For example, manipulated non-medical dataset 1101a can resemble a dataset from a percutaneous coronary intervention (PCI) procedure, while manipulated non-dataset 1101b can resemble a dataset from a pacemaker procedure.

Next, each of manipulated non-medical dataset 1101a and manipulated non-medical dataset 1101b are corrupted in S1105a and 1105b (respectively) to generate corresponding manipulated corrupted non-medical dataset 1103a and corresponding manipulated corrupted non-medical dataset 1103b (respectively). In S1107a, the manipulated non-medical dataset 1101a is used as output training data, and the corresponding manipulated corrupted non-medical dataset 1103a is used as input training data to generate trained deep-learning neural network 1109a. In S1107b, the manipulated non-medical dataset 1101b is used as output training data, and the corresponding manipulated corrupted non-medical dataset 1103b is used as input training data to generate a trained deep-learning neural network 1109b.

Upon producing deep-learning neural networks 1109a and 1109b, X-ray images 1111a can be input into deep-learning neural network 1109a, and X-ray images 1111b can be input into deep-learning neural network 1109b. X-ray images 1111a can be medical images that the manipulated non-medical dataset 1101a originally aimed to resemble, while X-ray images 1111b can be medical images that the manipulated non-medical dataset aimed to resemble. For example, if manipulated non-medical dataset 1101a resembled a PCI image, the X-ray images 1111a can be actual PCI images.

Next, the trained deep-learning neural networks 1109a and 1109b output high quality X-ray images 1113, where the high quality X-ray images 1113 include high quality versions of X-ray images 1111a and X-ray images 1111b. Each of the high quality X-ray images 1113 are corrupted in S1115 to generate their corresponding low quality X-ray images 1112.

In S1121, a deep-learning neural network is trained using the high quality X-ray images 1113 as output training data, and their corresponding low quality X-ray images 1112 as input training data. Upon completion of training in S1121, the trained deep-learning neural network can be used in the online X-ray image restoration process as described in S230.

Although the embodiment discussed with reference to FIG. 13 generated two deep-learning neural networks 1109a and 1109b using two manipulated non-medical datasets 1101a and 1101b, it can be appreciated that more than two non-medical datasets can be used to generated more than two deep-learning neural networks for outputting high quality X-ray images 1113 including more than two image types.

Figure 14:
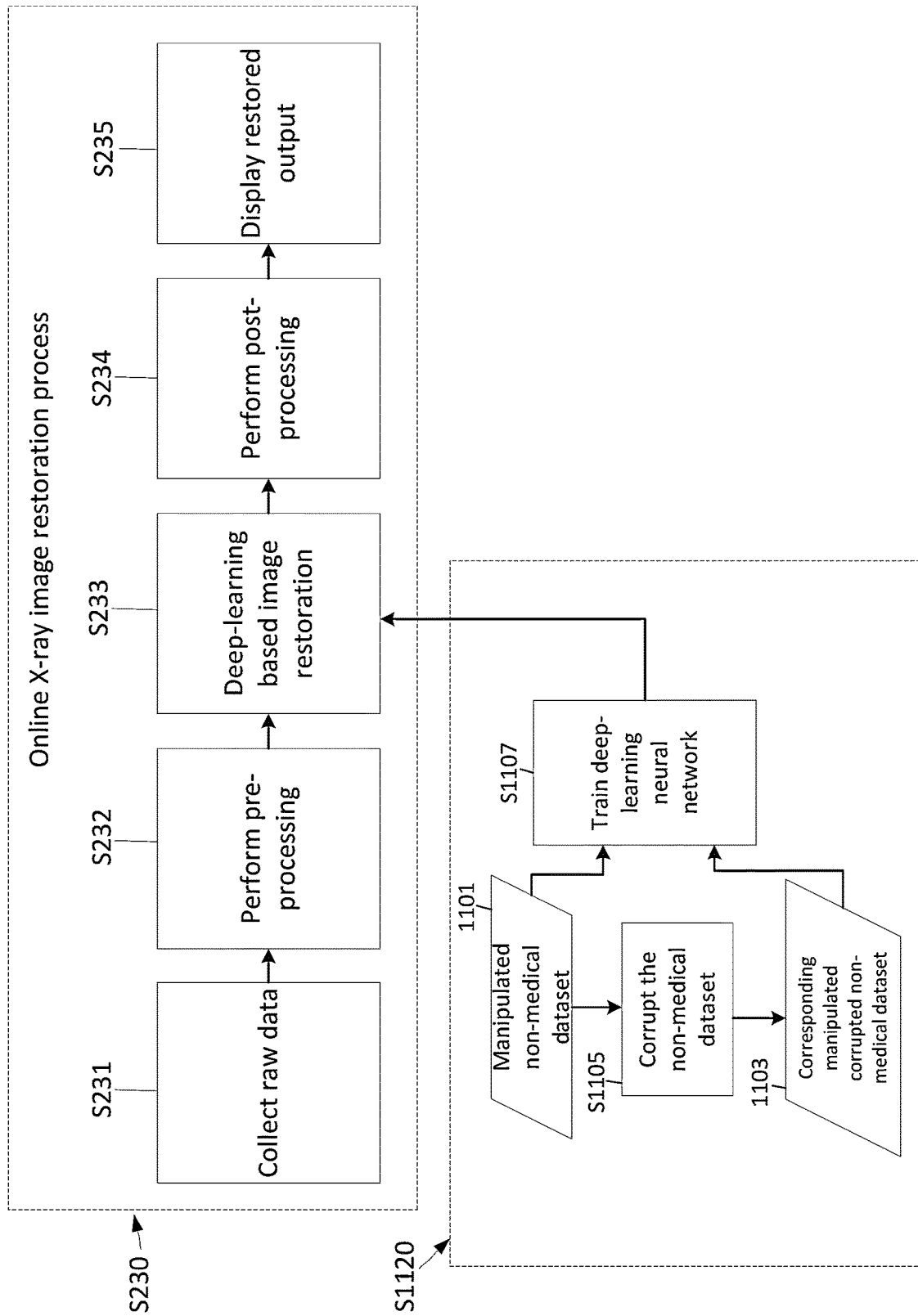
FIG. 14 is a workflow diagram illustrating the use of manipulated non-medical datasets to train a neural network for online X-ray image restoration.

FIG. 14 illustrates another workflow for offline data generation S1120, according to one embodiment. A manipulated non-medical dataset 1101 is obtained, as described in FIG. 12. In S1105, the manipulated non-medical dataset

1101 is corrupted to generate a corresponding corrupted manipulated non-medical dataset 1103, also as described in FIG. 12.

In S1107, a deep learning neural network is trained using the manipulated non-medical dataset 1101 as output learning data, and the corresponding corrupted manipulated non-medical dataset 1103 as input learning data. Upon completion of training in S1107, the deep-learning neural network can be used directly in deep-learning based image restoration of S233.

The method and system described herein can train and utilize a deep-learning neural network for creating higher quality images by removing noise and blur in real-time. The proposed techniques have various advantages that can result in an improved performance in both quality and speed. Examples of such advantages include, but are not limited to: these concepts can handle blurring and noise jointly; these concepts can be applied to X-ray imaging; these concepts can take into account physics and apparatus related variations; these concepts can use time-sequence data; these concepts can accelerate and improve the efficiency of the overall restoration process (e.g. by cropping an image, using multiple processors in series or parallel, pruning the deep-learning neural network, reducing the precision of the deep-learning neural network); these techniques are not limited to only cardiac purposes; and these techniques can utilize anatomical-based training datasets.

The method and system described herein can be implemented in a number of technologies but generally relate to imaging devices and processing circuitry for performing the processes described herein. In one embodiment, the processing circuitry (e.g., image processing circuitry and controller circuitry) is implemented as one of or as a combination of: an application specific integrated circuit (ASIC), a field programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include a computer processor and having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores. In an embodiment in which neural networks are used, the processing circuitry used to train the artificial neural network need not be the same as the processing circuitry used to implement the trained artificial neural network that performs the calibration described herein. For example, processor circuitry and memory may be used to produce a trained artificial neural network (e.g., as defined by its interconnections and weights), and an FPGA may be used to implement the trained artificial neural network. Moreover, the training and use of a trained artificial neural network may use a serial implementation or a parallel implementation for increased performance (e.g., by implementing the trained neural network on a parallel processor architecture such as a graphics processor architecture).

In the preceding description, specific details have been set forth relating to various components and processes. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Embodiments of the present disclosure may also be set forth in the following parentheticals.

(1) An X-ray diagnosis apparatus, comprising: processing circuitry configured to input a first image to a learned model; and output the first image with less noise and blur as a processed image, wherein the learned model is trained by using a second image as input learning data and a third image with less noise and blur than the second image as output learning data.

(2) The apparatus of (1), wherein the third image is obtained by deblurring and denoising the second image.

(3) The apparatus of any (1) to (2), wherein the second image is obtained by adding blur and noise to the third image.

(4) The apparatus of any (1) to (3), wherein the processing circuitry is further configured to prune the learned model after the learned model has been trained.

(5) The apparatus any (1) to (4), wherein the processing circuitry is further configured to reduce precision of the learned model after the learned model has been trained.

(6) The apparatus of any (1) to (5), wherein the learned model is a deep-learning neural network.

(7) The apparatus of any (1) to (6), wherein the first image, the second image, and the third image is an X-ray image.

(8) The apparatus of any (1) to (7), wherein the first image, the second image, and the third image is of a same anatomic structure.

(9) The apparatus of any (1) to (8), wherein the first image is a snippet of a full size image.

(10) The apparatus of any (1) to (9), wherein the third image is a manipulated non-medical dataset, and the second image is the manipulated non-medical dataset with corruption.

(11) The apparatus of any (1) to (10), wherein a second learned model is trained to take a fourth image as an input and output the third image, the second learned model trained using a manipulated non-medical dataset as output learning data, and the manipulated non-medical dataset with corruption as input learning data.

(12) A method for image restoration comprising: inputting a first image to a learned model; and outputting the first image with less noise and blur as a processed image, wherein the learned model is trained by using a second image as input learning data and a third image with less noise and blur than the second image as output learning data.

(13) The method of (12), wherein the second image is obtained by deblurring and denoising the first image.

(14) The method of any (12) to (13), wherein the first image is obtained by adding blur and noise to the second image.

(15) The method of any (12) to (14), further comprising: pruning the learned model after the learned model has been trained.

(16) The method of any (12) to (15), further comprising: reducing precision of the learned model after the learned model has been trained.

(17) The method of any (12) to (16), wherein the third image is a manipulated non-medical dataset, and the second image is the manipulated non-medical dataset with corruption.

(18) The method of any (12) to (17), wherein a second learned model is trained to take a fourth image as an input and output the third image, the second learned model trained using a manipulated non-medical dataset as output learning data, and the manipulated non-medical dataset with corruption as input learning data.

(19) The method of any (12) to (18), wherein the first image, the second image, and the third image is of a same anatomic structure.

(20) A non-transitory computer-readable medium including computer-readable instructions that, when executed by a computing system, cause the computing system to sort data by performing a method comprising: inputting a first image to a learned model; and outputting the first image with less noise and blur as a processed image, wherein the learned model is trained by using a second image as input learning data and a third image with less noise and blur than the second image as output learning data.

(21) A method for training a machine learning model, the method comprising: training the machine learning model by using a second image as input learning data and a third image with less noise and blur than the second image as output learning data, wherein the trained machine learning model receives a first image as an input image and output the first image with less noise and blur as a processed image.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the following claims.

The invention claimed is:

1. An X-ray diagnosis apparatus, comprising:
an X-ray tube configured to irradiate an imaging region of a subject with X-rays;
an X-ray detector configured to detect the X-rays; and
processing circuitry configured to
acquire, in a first process, a plurality of first X-ray images along a time sequence by detecting X-rays irradiated from the X-ray tube and passed through the subject;
input one of the plurality of first X-ray images to a learned model each time when the one of the plurality of first X-ray images is acquired; and
display, in a second process, an X-ray image, output from the learned model, with less noise and blur each time when the X-ray image is output, wherein the learned model is trained by using a second X-ray image as input learning data and a third X-ray image with less noise and blur than the second X-ray image as output learning data,
wherein the second process of displaying the output X-ray image is performed in parallel with the first process of acquiring the first X-ray images.

2. The apparatus of claim 1, wherein the third X-ray image is obtained by deblurring and denoising the second X-ray image.

3. The apparatus of claim 1, wherein the second X-ray image is obtained by adding blur and noise to the third X-ray image.

4. The apparatus of claim 1, wherein the processing circuitry is further configured to prune the learned model after the learned model has been trained.

5. The apparatus of claim 1, wherein the processing circuitry is further configured to reduce precision of the learned model after the learned model has been trained.

6. The apparatus of claim 1, wherein the learned model is a deep-learning neural network based on U-net.

7. The apparatus of claim 1, wherein the first X-ray image, the second X-ray image, and the third X-ray image are of a same anatomic structure.

8. The apparatus of claim 1, wherein the first X-ray image is a snippet of a full size image.

9. The apparatus of claim 1, wherein the third X-ray image is a manipulated non-medical dataset, and the second X-ray image is the manipulated non-medical dataset with corruption.

10. The apparatus of claim 1, wherein a second learned model is trained to take a fourth X-ray image as an input and output the third X-ray image, the second learned model trained using a manipulated non-medical dataset as output learning data, and the manipulated non-medical dataset with corruption as input learning data.

11. A method for image restoration, comprising:
acquiring, in a first process, a plurality of first X-ray images along a time sequence by detecting X-rays irradiated from an X-ray tube and passed through a subject using an X-ray detector;
inputting one of the plurality of first X-ray images to a learned model each time when the one of the plurality of first X-ray images is acquired; and
displaying, in a second process, an X-ray image, output from the learned model, with less noise and blur each time when the X-ray image is output, wherein the learned model is trained by using a second X-ray image as input learning data and a third X-ray image with less noise and blur than the second X-ray image as output learning data,
wherein the second process of displaying the output X-ray image is performed in parallel with the first process of acquiring the first X-ray images.

12. The method of claim 11, wherein the second X-ray image is obtained by deblurring and denoising the first X-ray image.

13. The method of claim 11, wherein the first X-ray image is obtained by adding blur and noise to the second X-ray image.

14. The method of claim 11, further comprising pruning the learned model after the learned model has been trained.

15. The method of claim 11, further comprising reducing precision of the learned model after the learned model has been trained.

16. The method of claim 11, wherein the third X-ray image is a manipulated non-medical dataset, and the second X-ray image is the manipulated non-medical dataset with corruption.

17. The method of claim 11, wherein a second learned model is trained to take a fourth X-ray image as an input and output the third X-ray image, the second learned model trained using a manipulated non-medical dataset as output learning data, and the manipulated non-medical dataset with corruption as input learning data.

18. The method of claim 11, wherein the first X-ray image, the second X-ray image, and the third X-ray image are of a same anatomic structure.

19. A non-transitory computer-readable medium including computer-readable instructions that, when executed by a computing system, cause the computing system to sort data by performing a method comprising:
    acquiring, in a first process, a plurality of first X-ray images along a time sequence by detecting X-rays irradiated from an X-ray tube and passed through a subject using an X-ray detector;
    inputting one of the plurality of first X-ray images to a learned model each time when the one of the plurality of first X-ray images is acquired; and
    displaying, in a second process, an X-ray image output from the learned model with less noise and blur each time when the image is output, wherein the learned model is trained by using a second X-ray image as input learning data and a third X-ray image with less noise and blur than the second X-ray image as output learning data,
    wherein the second process of displaying the output X-ray image is performed in parallel with the first process of acquiring the first X-ray images.

20. The apparatus of claim 1, wherein the processing, by the processing circuitry, of inputting the first X-ray image to the learned model and outputting the X-ray image is less computational consuming than a restoring algorithm for generating the third X-ray image.

21. The apparatus of claim 1, wherein the processing circuitry is further configured to input, to the learned model, the first X-ray image, of a time series of X-ray images, acquired using an X-ray apparatus, wherein a second learned model is trained to take a fourth X-ray image as an input and output the third X-ray image as the output learning data.

22. The apparatus of claim 1, wherein the processing circuitry is further configured to input, to the learned model, a plurality of a time series of X-ray images including the first X-ray image, and output the X-ray image with less noise and blur.

23. The apparatus of claim 22, wherein the processing circuitry is further configured to train the learned model using a loss function, which includes a first term being a noise-weighted difference between the time series of X-ray images and a corresponding target image, and a second term being a noise-weighted difference between the first X-ray image and other images in the plurality of the time series of X-ray images.

24. The apparatus of claim 1, wherein the noise includes at least one of quantum noise and electronic noise, the blur is caused from at least one of light spreading caused by scintillator, a finite focal spot size, and detector binning.

* * * * *